(12) United States Patent
Christou et al.

(10) Patent No.: US 7,019,197 B1
(45) Date of Patent: Mar. 28, 2006

(54) PESTICIDAL FUSIONS

(75) Inventors: Paul Christou, Norwich (GB); Luke Mehlo, Harare (ZW)

(73) Assignee: Fraunhofer-Gesellschaft Zur Foerderung Der Angewandten Forschung e. V, Munich (DE)

( * ) Notice: Subject to any disclaimer, the term of this patent is extended or adjusted under 35 U.S.C. 154(b) by 0 days.

(21) Appl. No.: 09/980,650

(22) PCT Filed: Apr. 27, 2000

(86) PCT No.: PCT/GB00/01633
§ 371 (c)(1),
(2), (4) Date: Apr. 5, 2002

(87) PCT Pub. No.: WO00/66755
PCT Pub. Date: Nov. 9, 2000

(30) Foreign Application Priority Data
Apr. 28, 1999 (GB) .................... 9909796

(51) Int. Cl.
*A01H 5/00* (2006.01)
*C12N 15/82* (2006.01)
*C12N 15/62* (2006.01)

(52) U.S. Cl. .............. 800/302; 800/279; 435/320.1; 435/418; 536/23.4

(58) Field of Classification Search .......... 800/298, 800/320.1, 279, 320.2, 302; 435/418, 320.1; 536/23.4
See application file for complete search history.

(56) References Cited

U.S. PATENT DOCUMENTS

| | | | |
|---|---|---|---|
| 4,664,911 A * | 5/1987 | Uhr et al. ........... | 424/182.1 |
| 5,290,914 A * | 3/1994 | Wilcox et al. ....... | 530/350 |
| 5,538,868 A * | 7/1996 | Horn et al. ......... | 435/91.1 |
| 5,668,255 A | 9/1997 | Murphy | |
| 5,763,245 A | 6/1998 | Greenplate | |

FOREIGN PATENT DOCUMENTS

| | | |
|---|---|---|
| WO | WO 96/10083 | 4/1996 |
| WO | WO 98/18820 | 5/1998 |

OTHER PUBLICATIONS

Lazar et al, 1988, Mol. Cell. Biol. 8:1247-1252.*
Hill et al, 1998, Biochem. Biophys. Res. Comm. 244:573-577.*
Gordon-Kamm et al, 1990, Plant Cell 2:603-618.*
Crickmore et al, 1998, Micro. Mole. Biol. Rev. 62:807-813.*
Youle et al, 1979, Proc. Natl. Acad. Sci 76:5559-5562.*
Dufresne et al, 2004, Nature Bio Technol 22:231-232.*
Barondes, 1988, TIBS 13:480-482.*
Rajemohan, F. et al. "*Bacillus thuringiensis* insecticidal proteins: molecular mode of action"; Progress in Nucleic Acid Research and Molecular Biology, 60: 1-27 (1998).
JP 06-1992295 A; Toagosei Chem Ind Co., Ltd. (1994) [Abstract].

* cited by examiner

*Primary Examiner*—Anne Kubelik
(74) *Attorney, Agent, or Firm*—Dann, Dorfman, Herrell & Skillman, P.C.

(57) ABSTRACT

Disclosed are polynucleotides encoding a pesticidal fusion polypeptide comprising (i) a toxin domain; and (ii) a heterologous binding domain capable of binding non-specifically to a cell membrane without disrupting that membrane. Preferably the toxin domain is derived from a *Bacillus thuringiensis* cry toxin (e.g. CryIA (b) or (c)) and the binding domain is derived from a lectin (e.g. ricin toxin B chain). The use of such fusions may help to inhibit the acquisition of resistance in a pest population treated with the polypeptide. A further aspect of the invention is a method of assessing the toxicity of a polypeptide to a pest species by expressing a nucleic acid encoding said polypeptide in a host cell from that species, observing the viability of the cell and correlating the results of the observation with the toxicity of the polypeptide, wherein the viability is determined by assessing esterase activity or membrane.

24 Claims, 21 Drawing Sheets

Fig. 3a

Figure 1:
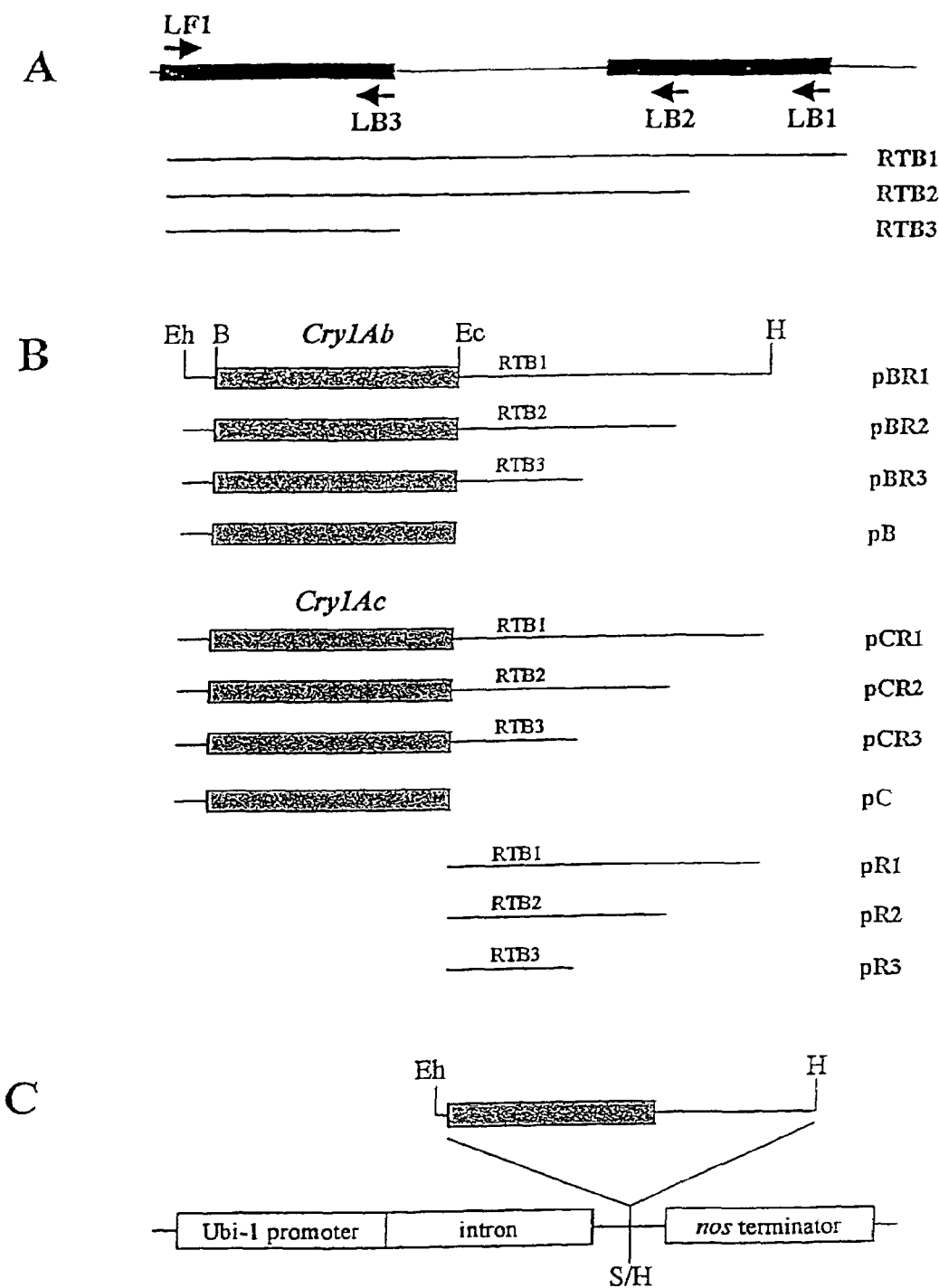

Nucleotide sequence of CryIA(b) in pFASTBAC1, Seq ID No 1.

```
   1 AAATAAGTAT TTTACTGTTT TCGTAACAGT TTTGTAATAA AAAAACCTAT
  51 AAATATTCCG GATTATTCAT ACCGTCCCAC CATCGGGCGC GGATCCATGG
 101 ACAACAACCC AAACATCAAC GAATGCATTC CATACAACTG CTTGAGTAAC
 151 CCAGAAGTTG AAGTACTTGG TGGAGAACGC ATTGAAACCG GTTACACTCC
 201 CATCGACATC TCCTTGTCCT TGACACAGTT TCTGCTCAGC GAGTTCGTGC
 251 CAGGTGCTGG GTTCGTTCTC GGACTAGTTG ACATCATCTG GGGTATCTTT
 301 GGTCCATCTC AATGGGATGC ATTCCTGGTG CAAATTGAGC AGTTGATCAA
 351 CCAGAGGATC GAAGAGTTCG CCAGGAACCA GGCCATCTCT AGGTTGGAAG
 401 GATTGAGCAA TCTCTACCAA ATCTATGCAG AGAGCTTCAG AGAGTGGGAA
 451 GCCGATCCTA CTAACCCAGC TCTCCGCGAG GAAATGCGTA TTCAATTCAA
 501 CGACATGAAC AGCGCCTTGA CCACAGCTAT CCCATTGTTC GCAGTCCAGA
 551 ACTACCAAGT TCCTCTCTTG TCCGTGTACG TTCAAGCAGC TAATCTTCAC
 601 CTCAGCGTGC TTCGAGACGT TAGCGTGTTT GGGCAAAGGT GGGGATTCGA
 651 TGCTGCAACC ATCAATAGCC GTTACAACGA CCTTACTAGG CTGATTGGAA
 701 ACTACACCGA CCACGCTGTT CGTTGGTACA ACACTGGCTT GGAGCGTGTC
 751 TGGGGTCCTG ATTCTAGAGA TTGGATTAGA TACAACCAGT TCAGGAGAGA
 801 ATTGACCCTC ACAGTTTTGG ACATTGTGTC TCTCTTCCCG AACTATGACT
 851 CCAGAACCTA CCCTATCCGT ACAGTGTCCC AACTTACCAG AGAAATCTAT
 901 ACTAACCCAG TTCTTGAGAA CTTCGACGGT AGCTTCCGTG GTTCTGCCCA
 951 AGGTATCGAA GGCTCCATCA GGAGCCCACA CTTGATGGAC ATCTTGAACA
1001 GCATAACTAT CTACACCGAT GCTCACAGAG GAGAGTATTA CTGGTCTGGA
1051 CACCAGATCA TGGCCTCTCC AGTTGGATTC AGCGGGCCCG AGTTTACCTT
1101 TCCTCTCTAT GGAACTATGG GAAACGCCGC TCCACAACAA CGTATCGTTG
1151 CTCAACTAGG TCAGGGTGTC TACAGAACCT TGTCTTCCAC CTTGTACAGA
1201 AGACCCTTCA ATATCGGTAT CAACAACCAG CAACTTTCCG TTCTTGACGG
1251 AACAGAGTTC GCCTATGGAA CCTCTTCTAA CTTGCCATCC GCTGTTTACA
1301 GAAAGAGCGG AACCGTTGAT TCCTTGGACG AAATCCCACC ACAGAACAAC
1351 AATGTGCCAC CCAGGCAAGG ATTCTCCCAC AGGTTGAGCC ACGTGTCCAT
1401 GTTCCGTTCC GGATTCAGCA ACAGTTCCGT GAGCATCATC AGAGCTCCTA
```

Fig. 3a (Cont ...)

```
1451  TGTTCTCATG GATTCATCGT AGTGCTGAGT TCAACAATAT CATTCCTTCC
1501  TCTCAAATCA CCCAAATCCC ATTGACCAAG TCTACTAACC TTGGATCTGG
1551  AACTTCTGTC GTGAAAGGAC CAGGCTTCAC AGGAGGTGAT ATTCTTAGAA
1601  GAACTTCTCC TGGCCAGATT AGCACCCTCA GAGTTAACAT CACTGCACCA
1651  CTTTCTCAAA GATATCGTGT CAGGATTCGT TACGCATCTA CCACTAACTT
1701  GCAATTCCAC ACCTCCATCG ACGGAAGGCC TATCAATCAG GGTAACTTCT
1751  CCGCAACCAT GTCAAGCGGC AGCAACTTGC AATCCGGCAG CTTCAGAACC
1801  GTCGGTTTCA CTACTCCTTT CAACTTCTCT AACGGATCAA GCGTTTTCAC
1851  CCTTAGCGCT CATGTGTTCA ATTCTGGCAA TGAAGTGTAC ATTGACCGTA
1901  TTGAGTTTGT GCCTGCCGAA GTTACCTTCG AGGCTGAGTA CTGAGAATTC
1951  AAAGGCCTAC GTCGACGAGC TCACTAGTCG CGGCCGCTTT CGAATCTAGA
2001  GCCTGCAGTC TCGAGGCATG CGGTACCAAG CTTGTCGAGA AGTACTAGAG
2051  GATCATAATC AG
```

Fig. 3b

Nucleotide sequence of CryIA(c) in pFASTBAC1  Seq ID No 2

```
   1  AAATAAGTAT TTTACTGTTT TCGTAACAGT TTTGTAATAA AAAAACCTAT
  51  AAATATTCCG GATTATTCAT ACCGTCCCAC CATCGGGCGC GGATCCATGG
 101  ACAACAACCC AAACATCAAC GAATGCATTC CATACAACTG CTTGAGTAAC
 151  CCAGAAGTTG AAGTACTTGG TGGAGAACGC ATTGAAACCG GTTACACTCC
 201  CATCGACATC TCCTTGTCCT TGACACAGTT TCTGCTCAGC GAGTTCGTGC
 251  CAGGTGCTGG GTTCGTTCTC GGACTAGTTG ACATCATCTG GGGTATCTTT
 301  GGTCCATCTC AATGGGATGC ATTCCTGGTG CAAATTGAGC AGTTGATCAA
 351  CCAGAGGATC GAAGAGTTCG CCAGGAACCA GGCCATCTCT AGGTTGGAAG
 401  GATTGAGCAA TCTCTACCAA ATCTATGCAG AGAGCTTCAG AGAGTGGGAA
 451  GCCGATCCTA CTAACCCAGC TCTCCGCGAG GAAATGCGTA TTCAATTCAA
 501  CGACATGAAC AGCGCCTTGA CCACAGCTAT CCCATTGTTC GCAGTCCAGA
 551  ACTACCAAGT TCCTCTCTTG TCCGTGTACG TTCAAGCAGC TAATCTTCAC
 601  CTCAGCGTGC TTCGAGACGT TAGCGTGTTT GGGCAAAGGT GGGGATTCGA
 651  TGCTGCAACC ATCAATAGCC GTTACAACGA CCTTACTAGG CTGATTGGAA
 701  ACTACACCGA CCACGCTGTT CGTTGGTACA ACACTGGCTT GGAGCGTGTC
 751  TGGGGTCCTG ATTCTAGAGA TTGGATTAGA TACAACCAGT TCAGGAGAGA
 801  ATTGACCCTC ACAGTTTTGG ACATTGTGTC TCTCTTCCCG AACTATGACT
 851  CCAGAACCTA CCCTATCCGT ACAGTGTCCC AACTTACCAG AGAAATCTAT
 901  ACTAACCCAG TTCTTGAGAA CTTCGACGGT AGCTTCCGTG GTTCTGCCCA
 951  AGGTATCGAA GGCTCCATCA GGAGCCCACA CTTGATGGAC ATCTTGAACA
1001  GCATAACTAT CTACACCGAT GCTCACAGAG GAGAGTATTA CTGGTCTGGA
1051  CACCAGATCA TGGCCTCTCC AGTTGGATTC AGCGGGCCCG AGTTTACCTT
1101  TCCTCTCTAT GGAACTATGG GAAACGCCGC TCCACAACAA CGTATCGTTG
1151  CTCAACTAGG TCAGGGTGTC TACAGAACCT TGTCTTCCAC CTTGTACAGA
1201  AGACCCTTCA ATATCGGTAT CAACAACCAG CAACTTTCCG TTCTTGACGG
1251  AACAGAGTTC GCCTATGGAA CCTCTTCTAA CTTGCCATCC GCTGTTTACA
1301  GAAAGAGCGG AACCGTTGAT TCCTTGGACG AAATCCCACC ACAGAACAAC
1351  AATGTGCCAC CCAGGCAAGG ATTCTCCCAC AGGTTGAGCC ACGTGTCCAT
1401  GTTCCGTTCC GGATTCAGCA ACAGTTCCGT GAGCATCATC AGAGCTCCTA
```

Fig. 3b (Cont...)

```
1451  TGTTCTCTTG GATACACCGT AGTGCTGAGT TCAACAACAT CATCGCATCC
1501  GATAGTATTA CTCAAATCCC TGCAGTGAAG GGAAACTTTC TCTTCAACGG
1551  TTCTGTCATT TCAGGACCAG GATTCACTGG TGGAGACCTC GTTAGACTCA
1601  ACAGCAGTGG AAATAACATT CAGAATAGAG GTATATTGA AGTTCCAATT
1651  CACTTCCCAT CCACATCTAC CAGATATAGA GTTCGTGTGA GGTATGCTTC
1701  TGTGACCCCT ATTCACCTCA ACGTTAATTG GGGTAATTCA TCCATCTTCT
1751  CCAATACAGT TCCAGCTACA GCTACCTCCT TGGATAATCT CCAATCCAGC
1801  GATTTCGGTT ACTTTGAAAG TGCCAATGCT TTTACATCTT CACTCGGTAA
1851  CATCGTGGGT GTTAGAAACT TTAGTGGGAC TGCAGGAGTG ATTATCGACA
1901  GATTCGAGTT CATTCCAGTT ACTGCAACAC TCGAGGCTGA ATGAGAATTC
1951  AAAGGCCTAC GTCGACGAGC TCACTAGTCG CGGCCGCTTT CGAATCTAGA
2001  GCCTGCAGTC TCGAGGCATG CGGTACCAAG CTTGTCGAGA AGTACTAGAG
2051  GATCATAATC AG
```

Fig. 3c

Nucleotide sequence of RTB1 in pFASTBAC1.    Seq ID No 3

```
  1  AAATAAGTAT TTTACTGTTT TCGTAACAGT TTTGTAATAA AAAAACCTAT
 51  AAATATTCCG GATTATTCAT ACCGTCCCAC CATCGGGCGC GGATCCCGGT
101  CCGAAGCGCG CGGAATTCAT GCTGATGTTT GTATGGATCC TGAGCCCATA
151  GTGCGTATCG TAGGTCGAAA TGGTCTATGT GTTGATGTTA GGGATGGAAG
201  ATTCCACAAC GGAAACGCAA TACAGTTGTG GCCATGCAAG TCTAATACAG
251  ATGCAAATCA GCTCTGGACT TTGAAAAGAG ACAATACTAT TCGATCTAAT
301  GGAAAGTGTT TAACTACTTA CGGGTACAGT CCGGGAGTCT ATGTGATGAT
351  CTATGATTGC AATACTGCTG CAACTGATGC CACCCGCTGG CAAATATGGG
401  ATAATGGAAC CATCATAAAT CCCAGATCTA GTCTAGTTTT AGCAGCGACA
451  TCAGGGAACA GTGGTACCAC ACTTACGGTG CAAACCAACA TTTATGCCGT
501  TAGTCAAGGT TGGCTTCCTA CTAATAATAC ACAACCTTTT GTTACAACCA
551  TTGTTGGGCT ATATGGTCTG TGCTTGCAAG CAAATAGTGG ACAAGTATGG
601  ATAGAGGACT GTAGCAGTGA AAAGGCTGAA CAACAGTGGG CTCTTTATGC
651  AGATGGTTCA ATACGTCCTC AGCAAAACCG AGATAATTGC CTTACAAGTG
701  ATTCTAATAT ACGGGAAACA GTTGTTAAGA TCCTCTCTTG TGGCCCTGCA
751  TCCTCTGGCC AACGATGGAT GTTCAAGAAT GATGGAACCA TTTTAAATTT
801  GTATAGTGGA TTGGTGTTAG ATGTGAGGCG ATCGGATCCG AGCCTTAAAC
851  AAATCATTCT TTACCCTCTC CATGGTGACC CAAACCAAAT ATGGTTACCA
901  TTATTTTGAT AGACAGATTA CAAGCTTGTC GAGAAGTACT AGAGGATCAT
951  AATCAG
```

Fig. 3d

Nucleotide sequence of RTB2 in pFASTBAC1     Seq ID No 4

```
  1  AAATAAGTAT TTTACTGTTT TCGTAACAGT TTTGTAATAA AAAAACCTAT
 51  AAATATTCCG GATTATTCAT ACCGTCCCAC CATCGGGCGC GGATCCCGGT
101  CCGAAGCGCG CGGAATTCAT GCTGATGTTT GTATGGATCC TGAGCCCATA
151  GTGCGTATCG TAGGTCGAAA TGGTCTATGT GTTGATGTTA GGGATGGAAG
201  ATTCCACAAC GGAAACGCAA TACAGTTGTG GCCATGCAAG TCTAATACAG
251  ATGCAAATCA GCTCTGGACT TTGAAAAGAG ACAATACTAT TCGATCTAAT
301  GGAAAGTGTT TAACTACTTA CGGGTACAGT CCGGGAGTCT ATGTGATGAT
351  CTATGATTGC AATACTGCTG CAACTGATGC CACCCGCTGG CAAATATGGG
401  ATAATGGAAC CATCATAAAT CCCAGATCTA GTCTAGTTTT AGCAGCGACA
451  TCAGGGAACA GTGGTACCAC ACTTACGGTG CAAACCAACA TTTATGCCGT
501  TAGTCAAGGT TGGCTTCCTA CTAATAATAC ACAACCTTTT GTTACAACCA
551  TTGTTGGGCT ATATGGTCTG TGCTTGCAAG CAAATAGTGG ACAAGTATGG
601  ATAGAGGACT GTAGCAGTGA AAAGGCTGAA CAACAGTGGG CTCTTTATGC
651  AGATGGTTCA ATACGTCCTC AGCAAAACCG AGATAATTGC CTTACAAGTG
701  ATTCTAATAT ACGGGAAACA GTTGTTAAGA TCCTCTCTTG TGGCCCTGCA
751  TCCTCTGGCC AACGATGGAT GTTCAAGAAT GATGGAACCA TTTTAAATTT
801  GTATAGTGGA TTGGTGTTAG ATGTGAAGCT TGTCGAGAAG TACTAGAGGA
851  TCATAATCAG
```

Fig. 3e

Nucleotide sequence of RTB3 in pFASTBAC1.   Seq ID No 5

```
  1  AAATAAGTAT TTTACTGTTT TCGTAACAGT TTTGTAATAA AAAAACCTAT
 51  AAATATTCCG GATTATTCAT ACCGTCCCAC CATCGGGCGC GGATCCCGGT
101  CCGAAGCGCG CGGAATTCAT GCTGATGTTT GTATGGATCC TGAGCCCATA
151  GTGCGTATCG TAGGTCGAAA TGGTCTATGT GTTGATGTTA GGGATGGAAG
201  ATTCCACAAC GGAAACGCAA TACAGTTGTG GCCATGCAAG TCTAATACAG
251  ATGCAAATCA GCTCTGGACT TTGAAAAGAG ACAATACTAT TCGATCTAAT
301  GGAAAGTGTT TAACTACTTA CGGGTACAGT CCGGGAGTCT ATGTGATGAT
351  CTATGATTGC AATACTGCTG CAACTGATGC CACCCGCTGG CAAATATGGG
401  ATAATGGAAC CATCATAAAT CCCAGATCTA GTCTAGTTTT AGCAGCGACA
451  TCAGGGAACA GTGGTACCAC ACTTACGGTG CAAACCAACA TTTATGCCGT
501  TAGTCAAGGT TGGCTTCCTA CTAATAATAC ACAACCTTTT GTTACAACCA
551  TTGTTGGGCT ATATGGTCTA AGCTTGTCGA GAAGTACTAG AGGATCATAA
601  TCAG
```

Fig. 3f

Nucleotide sequence of CryIA(b)-RTB1 in pFASTBAC1.   Seq ID No 6

```
   1  AAATAAGTAT TTTACTGTTT TCGTAACAGT TTTGTAATAA AAAAACCTAT
  51  AAATATTCCG GATTATTCAT ACCGTCCCAC CATCGGGCGC GGATCCATGG
 101  ACAACAACCC AAACATCAAC GAATGCATTC CATACAACTG CTTGAGTAAC
 151  CCAGAAGTTG AAGTACTTGG TGGAGAACGC ATTGAAACCG GTTACACTCC
 201  CATCGACATC TCCTTGTCCT TGACACAGTT TCTGCTCAGC GAGTTCGTGC
 251  CAGGTGCTGG GTTCGTTCTC GGACTAGTTG ACATCATCTG GGGTATCTTT
 301  GGTCCATCTC AATGGGATGC ATTCCTGGTG CAAATTGAGC AGTTGATCAA
 351  CCAGAGGATC GAAGAGTTCG CCAGGAACCA GGCCATCTCT AGGTTGGAAG
 401  GATTGAGCAA TCTCTACCAA ATCTATGCAG AGAGCTTCAG AGAGTGGGAA
 451  GCCGATCCTA CTAACCCAGC TCTCCGCGAG GAAATGCGTA TTCAATTCAA
 501  CGACATGAAC AGCGCCTTGA CCACAGCTAT CCCATTGTTC GCAGTCCAGA
 551  ACTACCAAGT TCCTCTCTTG TCCGTGTACG TTCAAGCAGC TAATCTTCAC
 601  CTCAGCGTGC TTCGAGACGT TAGCGTGTTT GGGCAAAGGT GGGGATTCGA
 651  TGCTGCAACC ATCAATAGCC GTTACAACGA CCTTACTAGG CTGATTGGAA
 701  ACTACACCGA CCACGCTGTT CGTTGGTACA ACACTGGCTT GGAGCGTGTC
 751  TGGGGTCCTG ATTCTAGAGA TTGGATTAGA TACAACCAGT TCAGGAGAGA
 801  ATTGACCCTC ACAGTTTTGG ACATTGTGTC TCTCTTCCCG AACTATGACT
 851  CCAGAACCTA CCCTATCCGT ACAGTGTCCC AACTTACCAG AGAAATCTAT
 901  ACTAACCCAG TTCTTGAGAA CTTCGACGGT AGCTTCCGTG GTTCTGCCCA
 951  AGGTATCGAA GGCTCCATCA GGAGCCCACA CTTGATGGAC ATCTTGAACA
1001  GCATAACTAT CTACACCGAT GCTCACAGAG GAGAGTATTA CTGGTCTGGA
1051  CACCAGATCA TGGCCTCTCC AGTTGGATTC AGCGGGCCCG AGTTTACCTT
1101  TCCTCTCTAT GGAACTATGG GAAACGCCGC TCCACAACAA CGTATCGTTG
1151  CTCAACTAGG TCAGGGTGTC TACAGAACCT TGTCTTCCAC CTTGTACAGA
```

Fig 3f (Cont ...)

```
1201  AGACCCTTCA ATATCGGTAT CAACAACCAG CAACTTTCCG TTCTTGACGG
1251  AACAGAGTTC GCCTATGGAA CCTCTTCTAA CTTGCCATCG GCTGTTTACA
1301  GAAAGAGCGG AACCGTTGAT TCCTTGGACG AAATCCCACC ACAGAACAAC
1351  AATGTGCCAC CCAGGCAAGG ATTCTCCCAC AGGTTGAGCC ACGTGTCCAT
1401  GTTCCGTTCC GGATTCAGCA ACAGTTCCGT GAGCATCATC AGAGCTCCTA
1451  TGTTCTCATG GATTCATCGT AGTGCTGAGT TCAACAATAT CATTCCTTCC
1501  TCTCAAATCA CCCAAATCCC ATTGACCAAG TCTACTAACC TTGGATCTGG
1551  AACTTCTGTC GTGAAAGGAC CAGGCTTCAC AGGAGGTGAT ATTCTTAGAA
1601  GAACTTCTCC TGGCCAGATT AGCACCCTCA GAGTTAACAT CACTGCACCA
1651  CTTTCTCAAA GATATCGTGT CAGGATTCGT TACGCATCTA CCACTAACTT
1701  GCAATTCCAC ACCTCCATCG ACGGAAGGCC TATCAATCAG GGTAACTTCT
1751  CCGCAACCAT GTCAAGCGGC AGCAACTTGC AATCCGGCAG CTTCAGAACC
1801  GTCGGTTTCA CTACTCCTTT CAACTTCTCT AACGGATCAA GCGTTTTCAC
1851  CCTTAGCGCT CATGTGTTCA ATTCTGGCAA TGAAGTGTAC ATTGACCGTA
1901  TTGAGTTTGT GCCTGCCGAA GTTACCTTCG AGGCTGAGTA CTGAGAATTC
1951  ATGCTGATGT TTGTATGGAT CCTGAGCCCA TAGTGCGTAT CGTAGGTCGA
2001  AATGGTCTAT GTGTTGATGT TAGGGATGGA AGATTCCACA ACGGAAACGC
2051  AATACAGTTG TGGCCATGCA AGTCTAATAC AGATGCAAAT CAGCTCTGGA
2101  CTTTGAAAAG AGACAATACT ATTCGATCTA ATGGAAAGTG TTTAACTACT
2151  TACGGGTACA GTCCGGGAGT CTATGTGATG ATCTATGATT GCAATACTGC
2201  TGCAACTGAT GCCACCCGCT GGCAAATATG GGATAATGGA ACCATCATAA
2251  ATCCCAGATC TAGTCTAGTT TTAGCAGCGA CATCAGGGAA CAGTGGTACC
2301  ACACTTACGG TGCAAACCAA CATTTATGCC GTTAGTCAAG GTTGGCTTCC
2351  TACTAATAAT ACACAACCTT TTGTTACAAC CATTGTTGGG CTATATGGTC
2401  TGTGCTTGCA AGCAAATAGT GGACAAGTAT GGATAGAGGA CTGTAGCAGT
2451  GAAAAGGCTG AACAACAGTG GGCTCTTTAT GCAGATGGTT CAATACGTCC
2501  TCAGCAAAAC CGAGATAATT GCCTTACAAG TGATTCTAAT ATACGGGAAA
2551  CAGTTGTTAA GATCCTCTCT TGTGGCCCTG CATCCTCTGG CCAACGATGG
2601  ATGTTCAAGA ATGATGGAAC CATTTTAAAT TTGTATAGTG GATTGGTGTT
2651  AGATGTGAGG CGATCGGATC CGAGCCTTAA ACAAATCATT CTTTACCCTC
2701  TCCATGGTGA CCCAAACCAA ATATGGTTAC CATTATTTTG ATAGACAGAT
2751  TACAAGCTTG TCGAGAAGTA CTAGAGGATC ATAATCAG
```

Fig. 3g

Nucleotide sequence of CryIA(b)-RTB2 in pFASTBAC1.: Seq

Fig. 3g (Cont ...)

```
1201 AGACCCTTCA ATATCGGTAT CAACAACCAG CAACTTTCCG TTCTTGACGG
1251 AACAGAGTTC GCCTATGGAA CCTCTTCTAA CTTGCCATCC GCTGTTTACA
1301 GAAAGAGCGG AACCGTTGAT TCCTTGGACG AAATCCCACC ACAGAACAAC
1351 AATGTGCCAC CCAGGCAAGG ATTCTCCCAC AGGTTGAGCC ACGTGTCCAT
1401 GTTCCGTTCC GGATTCAGCA ACAGTTCCGT GAGCATCATC AGAGCTCCTA
1451 TGTTCTCATG GATTCATCGT AGTGCTGAGT TCAACAATAT CATTCCTTCC
1501 TCTCAAATCA CCCAAATCCC ATTGACCAAG TCTACTAACC TTGGATCTGG
1551 AACTTCTGTC GTGAAAGGAC CAGGCTTCAC AGGAGGTGAT ATTCTTAGAA
1601 GAACTTCTCC TGGCCAGATT AGCACCCTCA GAGTTAACAT CACTGCACCA
1651 CTTTCTCAAA GATATCGTGT CAGGATTCGT TACGCATCTA CCACTAACTT
1701 GCAATTCCAC ACCTCCATCG ACGGAAGGCC TATCAATCAG GGTAACTTCT
1751 CCGCAACCAT GTCAAGCGGC AGCAACTTGC AATCCGGCAG CTTCAGAACC
1801 GTCGGTTTCA CTACTCCTTT CAACTTCTCT AACGGATCAA GCGTTTTCAC
1851 CCTTAGCGCT CATGTGTTCA ATTCTGGCAA TGAAGTGTAC ATTGACCGTA
1901 TTGAGTTTGT GCCTGCCGAA GTTACCTTCG AGGCTGAGTA CTGAGAATTC
1951 ATGCTGATGT TTGTATGGAT CCTGAGCCCA TAGTGCGTAT CGTAGGTCGA
2001 AATGGTCTAT GTGTTGATGT TAGGGATGGA AGATTCCACA ACGGAAACGC
2051 AATACAGTTG TGGCCATGCA AGTCTAATAC AGATGCAAAT CAGCTCTGGA
2101 CTTTGAAAAG AGACAATACT ATTCGATCTA ATGGAAAGTG TTTAACTACT
2151 TACGGGTACA GTCCGGGAGT CTATGTGATG ATCTATGATT GCAATACTGC
2201 TGCAACTGAT GCCACCCGCT GGCAAATATG GGATAATGGA ACCATCATAA
2251 ATCCCAGATC TAGTCTAGTT TTAGCAGCGA CATCAGGGAA CAGTGGTACC
2301 ACACTTACGG TGCAAACCAA CATTTATGCC GTTAGTCAAG GTTGGCTTCC
2351 TACTAATAAT ACACAACCTT TTGTTACAAC CATTGTTGGG CTATATGGTC
2401 TGTGCTTGCA AGCAAATAGT GGACAAGTAT GGATAGAGGA CTGTAGCAGT
2451 GAAAAGGCTG AACAACAGTG GGCTCTTTAT GCAGATGGTT CAATACGTCC
2501 TCAGCAAAAC CGAGATAATT GCCTTACAAG TGATTCTAAT ATACGGGAAA
2551 CAGTTGTTAA GATCCTCTCT TGTGGCCCTG CATCCTCTGG CCAACGATGG
2601 ATGTTCAAGA ATGATGGAAC CATTTTAAAT TTGTATAGTG GATTGGTGTT
2651 AGATGTGAAG CTTGTCGAGA AGTACTAGAG GATCATAATC AG
```

Fig. 3h

Nucleotide sequence of CryIA(b)-RTB3 in pFASTBAC1 : Seq ID No 8

```
   1  AAATAAGTAT TTTACTGTTT TCGTAACAGT TTTGTAATAA AAAAACCTAT
  51  AAATATTCCG GATTATTCAT ACCGTCCCAC CATCGGGCGC GGATCCATGG
 101  ACAACAACCC AAACATCAAC GAATGCATTC CATACAACTG CTTGAGTAAC
 151  CCAGAAGTTG AAGTACTTGG TGGAGAACGC ATTGAAACCG GTTACACTCC
 201  CATCGACATC TCCTTGTCCT TGACACAGTT TCTGCTCAGC GAGTTCGTGC
 251  CAGGTGCTGG GTTCGTTCTC GGACTAGTTG ACATCATCTG GGGTATCTTT
 301  GGTCCATCTC AATGGGATGC ATTCCTGGTG CAAATTGAGC AGTTGATCAA
 351  CCAGAGGATC GAAGAGTTCG CCAGGAACCA GGCCATCTCT AGGTTGGAAG
 401  GATTGAGCAA TCTCTACCAA ATCTATGCAG AGAGCTTCAG AGAGTGGGAA
 451  GCCGATCCTA CTAACCCAGC TCTCCGCGAG GAAATGCGTA TTCAATTCAA
 501  CGACATGAAC AGCGCCTTGA CCACAGCTAT CCCATTGTTC GCAGTCCAGA
 551  ACTACCAAGT TCCTCTCTTG TCCGTGTACG TTCAAGCAGC TAATCTTCAC
 601  CTCAGCGTGC TTCGAGACGT TAGCGTGTTT GGGCAAAGGT GGGGATTCGA
 651  TGCTGCAACC ATCAATAGCC GTTACAACGA CCTTACTAGG CTGATTGGAA
 701  ACTACACCGA CCACGCTGTT CGTTGGTACA ACACTGGCTT GGAGCGTGTC
 751  TGGGGTCCTG ATTCTAGAGA TTGGATTAGA TACAACCAGT TCAGGAGAGA
 801  ATTGACCCTC ACAGTTTTGG ACATTGTGTC TCTCTTCCCG AACTATGACT
 851  CCAGAACCTA CCCTATCCGT ACAGTGTCCC AACTTACCAG AGAAATCTAT
 901  ACTAACCCAG TTCTTGAGAA CTTCGACGGT AGCTTCCGTG GTTCTGCCCA
 951  AGGTATCGAA GGCTCCATCA GGAGCCCACA CTTGATGGAC ATCTTGAACA
1001  GCATAACTAT CTACACCGAT GCTCACAGAG GAGAGTATTA CTGGTCTGGA
1051  CACCAGATCA TGGCCTCTCC AGTTGGATTC AGCGGGCCCG AGTTTACCTT
1101  TCCTCTCTAT GGAACTATGG GAAACGCCGC TCCACAACAA CGTATCGTTG
1151  CTCAACTAGG TCAGGGTGTC TACAGAACCT TGTCTTCCAC CTTGTACAGA
```

Fig. 3h (Cont ...)

```
1201  AGACCCTTCA ATATCGGTAT CAACAACCAG CAACTTTCCG TTCTTGACGG
1251  AACAGAGTTC GCCTATGGAA CCTCTTCTAA CTTGCCATCC GCTGTTTACA
1301  GAAAGAGCGG AACCGTTGAT TCCTTGGACG AAATCCCACC ACAGAACAAC
1351  AATGTGCCAC CCAGGCAAGG ATTCTCCAC AGGTTGAGCC ACGTGTCCAT
1401  GTTCCGTTCC GGATTCAGCA ACAGTTCCGT GAGCATCATC AGAGCTCCTA
1451  TGTTCTCATG GATTCATCGT AGTGCTGAGT TCAACAATAT CATTCCTTCC
1501  TCTCAAATCA CCCAAATCCC ATTGACCAAG TCTACTAACC TTGGATCTGG
1551  AACTTCTGTC GTGAAAGGAC CAGGCTTCAC AGGAGGTGAT ATTCTTAGAA
1601  GAACTTCTCC TGGCCAGATT AGCACCCTCA GAGTTAACAT CACTGCACCA
1651  CTTTCTCAAA GATATCGTGT CAGGATTCGT TACGCATCTA CCACTAACTT
1701  GCAATTCCAC ACCTCCATCG ACGGAAGGCC TATCAATCAG GGTAACTTCT
1751  CCGCAACCAT GTCAAGCGGC AGCAACTTGC AATCCGGCAG CTTCAGAACC
1801  GTCGGTTTCA CTACTCCTTT CAACTTCTCT AACGGATCAA GCGTTTTCAC
1851  CCTTAGCGCT CATGTGTTCA ATTCTGGCAA TGAAGTGTAC ATTGACCGTA
1901  TTGAGTTTGT GCCTGCCGAA GTTACCTTCG AGGCTGAGTA CTGAGAATTC
1951  ATGCTGATGT TTGTATGGAT CCTGAGCCCA TAGTGCGTAT CGTAGGTCGA
2001  AATGGTCTAT GTGTTGATGT TAGGGATGGA AGATTCCACA ACGGAAACGC
2051  AATACAGTTG TGGCCATGCA AGTCTAATAC AGATGCAAAT CAGCTCTGGA
2101  CTTTGAAAAG AGACAATACT ATTCGATCTA ATGGAAAGTG TTTAACTACT
2151  TACGGGTACA GTCCGGGAGT CTATGTGATG ATCTATGATT GCAATACTGC
2201  TGCAACTGAT GCCACCCGCT GGCAAATATG GGATAATGGA ACCATCATAA
2251  ATCCCAGATC TAGTCTAGTT TTAGCAGCGA CATCAGGGAA CAGTGGTACC
2301  ACACTTACGG TGCAAACCAA CATTTATGCC GTTAGTCAAG GTTGGCTTCC
2351  TACTAATAAT ACACAACCTT TTGTTACAAC CATTGTTGGG CTATATGGTC
2401  TAAGCTTGTC GAGAAGTACT AGAGGATCAT AATCAG
```

Fig. 3i

Nucleotide sequence of CryIA(c)-RTB1 in pFASTBAC1 : Seq ID No 9

```
   1  AAATAAGTAT TTTACTGTTT TCGTAACAGT TTTGTAATAA AAAAACCTAT
  51  AAATATTCCG GATTATTCAT ACCGTCCCAC CATCGGGCGC GGATCCATGG
 101  ACAACAACCC AAACATCAAC GAATGCATTC CATACAACTG CTTGAGTAAC
 151  CCAGAAGTTG AAGTACTTGG TGGAGAACGC ATTGAAACCG GTTACACTCC
 201  CATCGACATC TCCTTGTCCT TGACACAGTT TCTGCTCAGC GAGTTCGTGC
 251  CAGGTGCTGG GTTCGTTCTC GGACTAGTTG ACATCATCTG GGGTATCTTT
 301  GGTCCATCTC AATGGGATGC ATTCCTGGTG CAAATTGAGC AGTTGATCAA
 351  CCAGAGGATC GAAGAGTTCG CCAGGAACCA GGCCATCTCT AGGTTGGAAG
 401  GATTGAGCAA TCTCTACCAA ATCTATGCAG AGAGCTTCAG AGAGTGGGAA
 451  GCCGATCCTA CTAACCCAGC TCTCCGCGAG GAAATGCGTA TTCAATTCAA
 501  CGACATGAAC AGCGCCTTGA CCACAGCTAT CCCATTGTTC GCAGTCCAGA
 551  ACTACCAAGT TCCTCTCTTG TCCGTGTACG TTCAAGCAGC TAATCTTCAC
 601  CTCAGCGTGC TTCGAGACGT TAGCGTGTTT GGGCAAAGGT GGGGATTCGA
 651  TGCTGCAACC ATCAATAGCC GTTACAACGA CCTTACTAGG CTGATTGGAA
 701  ACTACACCGA CCACGCTGTT CGTTGGTACA ACACTGGCTT GGAGCGTGTC
 751  TGGGGTCCTG ATTCTAGAGA TTGGATTAGA TACAACCAGT TCAGGAGAGA
 801  ATTGACCCTC ACAGTTTTGG ACATTGTGTC TCTCTTCCCG AACTATGACT
 851  CCAGAACCTA CCCTATCCGT ACAGTGTCCC AACTTACCAG AGAAATCTAT
 901  ACTAACCCAG TTCTTGAGAA CTTCGACGGT AGCTTCCGTG GTTCTGCCCA
 951  AGGTATCGAA GGCTCCATCA GGAGCCCACA CTTGATGGAC ATCTTGAACA
1001  GCATAACTAT CTACACCGAT GCTCACAGAG GAGAGTATTA CTGGTCTGGA
1051  CACCAGATCA TGGCCTCTCC AGTTGGATTC AGCGGGCCCG AGTTTACCTT
1101  TCCTCTCTAT GGAACTATGG GAAACGCCGC TCCACAACAA CGTATCGTTG
1151  CTCAACTAGG TCAGGGTGTC TACAGAACCT TGTCTTCCAC CTTGTACAGA
```

Fig. 3i (Cont ...)

```
1201  AGACCCTTCA ATATCGGTAT CAACAACCAG CAACTTTCCG TTCTTGACGG
1251  AACAGAGTTC GCCTATGGAA CCTCTTCTAA CTTGCCATCC GCTGTTTACA
1301  GAAAGAGCGG AACCGTTGAT TCCTTGGACG AAATCCCACC ACAGAACAAC
1351  AATGTGCCAC CCAGGCAAGG ATTCTCCCAC AGGTTGAGCC ACGTGTCCAT
1401  GTTCCGTTCC GGATTCAGCA ACAGTTCCGT GAGCATCATC AGAGCTCCTA
1451  TGTTCTCTTG GATACACCGT AGTGCTGAGT TCAACAACAT CATCGCATCC
1501  GATAGTATTA CTCAAATCCC TGCAGTGAAG GGAAACTTTC TCTTCAACGG
1551  TTCTGTCATT TCAGGACCAG GATTCACTGG TGGAGACCTC GTTAGACTCA
1601  ACAGCAGTGG AAATAACATT CAGAATAGAG GGTATATTGA AGTTCCAATT
1651  CACTTCCCAT CCACATCTAC CAGATATAGA GTTCGTGTGA GGTATGCTTC
1701  TGTGACCCCT ATTCACCTCA ACGTTAATTG GGGTAATTCA TCCATCTTCT
1751  CCAATACAGT TCCAGCTACA GCTACCTCCT TGGATAATCT CCAATCCAGC
1801  GATTTCGGTT ACTTTGAAAG TGCCAATGCT TTTACATCTT CACTCGGTAA
1851  CATCGTGGGT GTTAGAAACT TTAGTGGGAC TGCAGGAGTG ATTATCGACA
1901  GATTCGAGTT CATTCCAGTT ACTGCAACAC TCGAGGCTGA ATGAGAATTC
1951  ATGCTGATGT TTGTATGGAT CCTGAGCCCA TAGTGCGTAT CGTAGGTCGA
2001  AATGGTCTAT GTGTTGATGT TAGGGATGGA AGATTCCACA ACGGAAACGC
2051  AATACAGTTG TGGCCATGCA AGTCTAATAC AGATGCAAAT CAGCTCTGGA
2101  CTTTGAAAAG AGACAATACT ATTCGATCTA ATGGAAAGTG TTTAACTACT
2151  TACGGGTACA GTCCGGGAGT CTATGTGATG ATCTATGATT GCAATACTGC
2201  TGCAACTGAT GCCACCCGCT GGCAAATATG GGATAATGGA ACCATCATAA
2251  ATCCCAGATC TAGTCTAGTT TTAGCAGCGA CATCAGGGAA CAGTGGTACC
2301  ACACTTACGG TGCAAACCAA CATTTATGCC GTTAGTCAAG GTTGGCTTCC
2351  TACTAATAAT ACACAACCTT TTGTTACAAC CATTGTTGGG CTATATGGTC
2401  TGTGCTTGCA AGCAAATAGT GGACAAGTAT GGATAGAGGA CTGTAGCAGT
2451  GAAAAGGCTG AACAACAGTG GGCTCTTTAT GCAGATGGTT CAATACGTCC
2501  TCAGCAAAAC CGAGATAATT GCCTTACAAG TGATTCTAAT ATACGGGAAA
2551  CAGTTGTTAA GATCCTCTCT TGTGGCCCTG CATCCTCTGG CCAACGATGG
2601  ATGTTCAAGA ATGATGGAAC CATTTTAAAT TTGTATAGTG GATTGGTGTT
2651  AGATGTGAGG CGATCGGATC CGAGCCTTAA ACAAATCATT CTTTACCCTC
2701  TCCATGGTGA CCCAAACCAA ATATGGTTAC CATTATTTTG ATAGACAGAT
2751  TACAAGCTTG TCGAGAAGTA CTAGAGGATC ATAATCAG
```

Fig. 3j

Nucleotide sequence of CryIA(c)-RTB2 in pFASTBAC1 : Seq ID No 10

```
   1  AAATAAGTAT TTTACTGTTT TCGTAACAGT TTTGTAATAA AAAAACCTAT
  51  AAATATTCCG GATTATTCAT ACCGTCCCAC CATCGGGCGC GGATCCATGG
 101  ACAACAACCC AAACATCAAC GAATGCATTC CATACAACTG CTTGAGTAAC
 151  CCAGAAGTTG AAGTACTTGG TGGAGAACGC ATTGAAACCG GTTACACTCC
 201  CATCGACATC TCCTTGTCCT TGACACAGTT TCTGCTCAGC GAGTTCGTGC
 251  CAGGTGCTGG GTTCGTTCTC GGACTAGTTG ACATCATCTG GGGTATCTTT
 301  GGTCCATCTC AATGGGATGC ATTCCTGGTG CAAATTGAGC AGTTGATCAA
 351  CCAGAGGATC GAAGAGTTCG CCAGGAACCA GGCCATCTCT AGGTTGGAAG
 401  GATTGAGCAA TCTCTACCAA ATCTATGCAG AGAGCTTCAG AGAGTGGGAA
 451  GCCGATCCTA CTAACCCAGC TCTCCGCGAG GAAATGCGTA TTCAATTCAA
 501  CGACATGAAC AGCGCCTTGA CCACAGCTAT CCCATTGTTC GCAGTCCAGA
 551  ACTACCAAGT TCCTCTCTTG TCCGTGTACG TTCAAGCAGC TAATCTTCAC
 601  CTCAGCGTGC TTCGAGACGT TAGCGTGTTT GGGCAAAGGT GGGGATTCGA
 651  TGCTGCAACC ATCAATAGCC GTTACAACGA CCTTACTAGG CTGATTGGAA
 701  ACTACACCGA CCACGCTGTT CGTTGGTACA ACACTGGCTT GGAGCGTGTC
 751  TGGGGTCCTG ATTCTAGAGA TTGGATTAGA TACAACCAGT TCAGGAGAGA
 801  ATTGACCCTC ACAGTTTTGG ACATTGTGTC TCTCTTCCCG AACTATGACT
 851  CCAGAACCTA CCCTATCCGT ACAGTGTCCC AACTTACCAG AGAAATCTAT
 901  ACTAACCCAG TTCTTGAGAA CTTCGACGGT AGCTTCCGTG GTTCTGCCCA
 951  AGGTATCGAA GGCTCCATCA GGAGCCCACA CTTGATGGAC ATCTTGAACA
1001  GCATAACTAT CTACACCGAT GCTCACAGAG GAGAGTATTA CTGGTCTGGA
1051  CACCAGATCA TGGCCTCTCC AGTTGGATTC AGCGGGCCCG AGTTTACCTT
1101  TCCTCTCTAT GGAACTATGG GAAACGCCGC TCCACAACAA CGTATCGTTG
1151  CTCAACTAGG TCAGGGTGTC TACAGAACCT TGTCTTCCAC CTTGTACAGA
```

Fig. 3j (Cont...)

```
1201  AGACCCTTCA ATATCGGTAT CAACAACCAG CAACTTTCCG TTCTTGACGG
1251  AACAGAGTTC GCCTATGGAA CCTCTTCTAA CTTGCCATCC GCTGTTTACA
1301  GAAAGAGCGG AACCGTTGAT TCCTTGGACG AAATCCCACC ACAGAACAAC
1351  AATGTGCCAC CCAGGCAAGG ATTCTCCCAC AGGTTGAGCC ACGTGTCCAT
1401  GTTCCGTTCC GGATTCAGCA ACAGTTCCGT GAGCATCATC AGAGCTCCTA
1451  TGTTCTCTTG GATACACCGT AGTGCTGAGT TCAACAACAT CATCGCATCC
1501  GATAGTATTA CTCAAATCCC TGCAGTGAAG GGAAACTTTC TCTTCAACGG
1551  TTCTGTCATT TCAGGACCAG GATTCACTGG TGGAGACCTC GTTAGACTCA
1601  ACAGCAGTGG AAATAACATT CAGAATAGAG GGTATATTGA AGTTCCAATT
1651  CACTTCCCAT CCACATCTAC CAGATATAGA GTTCGTGTGA GGTATGCTTC
1701  TGTGACCCCT ATTCACCTCA ACGTTAATTG GGGTAATTCA TCCATCTTCT
1751  CCAATACAGT TCCAGCTACA GCTACCTCCT TGGATAATCT CCAATCCAGC
1801  GATTTCGGTT ACTTTGAAAG TGCCAATGCT TTTACATCTT CACTCGGTAA
1851  CATCGTGGGT GTTAGAAACT TTAGTGGGAC TGCAGGAGTG ATTATCGACA
1901  GATTCGAGTT CATTCCAGTT ACTGCAACAC TCGAGGCTGA ATGAGAATTC
1951  ATGCTGATGT TTGTATGGAT CCTGAGCCCA TAGTGCGTAT CGTAGGTCGA
2001  AATGGTCTAT GTGTTGATGT TAGGGATGGA AGATTCCACA ACGGAAACGC
2051  AATACAGTTG TGGCCATGCA AGTCTAATAC AGATGCAAAT CAGCTCTGGA
2101  CTTTGAAAAG AGACAATACT ATTCGATCTA ATGGAAAGTG TTTAACTACT
2151  TACGGGTACA GTCCGGGAGT CTATGTGATG ATCTATGATT GCAATACTGC
2201  TGCAACTGAT GCCACCCGCT GGCAAATATG GATAATGGA ACCATCATAA
2251  ATCCCAGATC TAGTCTAGTT TTAGCAGCGA CATCAGGGAA CAGTGGTACC
2301  ACACTTACGG TGCAAACCAA CATTTATGCC GTTAGTCAAG GTTGGCTTCC
2351  TACTAATAAT ACACAACCTT TTGTTACAAC CATTGTTGGG CTATATGGTC
2401  TGTGCTTGCA AGCAAATAGT GGACAAGTAT GGATAGAGGA CTGTAGCAGT
2451  GAAAAGGCTG AACAACAGTG GGCTCTTTAT GCAGATGGTT CAATACGTCC
2501  TCAGCAAAAC CGAGATAATT GCCTTACAAG TGATTCTAAT ATACGGGAAA
2551  CAGTTGTTAA GATCCTCTCT TGTGGCCCTG CATCCTCTGG CCAACGATGG
2601  ATGTTCAAGA ATGATGGAAC CATTTTAAAT TTGTATAGTG GATTGGTGTT
2651  AGATGTGAAG CTTGTCGAGA AGTACTAGAG GATCATAATC AG
```

Fig. 3k

Nucleotide sequence of CryIA(c)-RTB3 in pFASTBAC1.: Seq ID No 11

```
   1  AAATAAGTAT TTTACTGTTT TCGTAACAGT TTTGTAATAA AAAAACCTAT
  51  AAATATTCCG GATTATTCAT ACCGTCCCAC CATCGGGCGC GGATCCATGG
 101  ACAACAACCC AAACATCAAC GAATGCATTC CATACAACTG CTTGAGTAAC
 151  CCAGAAGTTG AAGTACTTGG TGGAGAACGC ATTGAAACCG GTTACACTCC
 201  CATCGACATC TCCTTGTCCT TGACACAGTT TCTGCTCAGC GAGTTCGTGC
 251  CAGGTGCTGG GTTCGTTCTC GGACTAGTTG ACATCATCTG GGGTATCTTT
 301  GGTCCATCTC AATGGGATGC ATTCCTGGTG CAAATTGAGC AGTTGATCAA
 351  CCAGAGGATC GAAGAGTTCG CCAGGAACCA GGCCATCTCT AGGTTGGAAG
 401  GATTGAGCAA TCTCTACCAA ATCTATGCAG AGAGCTTCAG AGAGTGGGAA
 451  GCCGATCCTA CTAACCCAGC TCTCCGCGAG GAAATGCGTA TTCAATTCAA
 501  CGACATGAAC AGCGCCTTGA CCACAGCTAT CCCATTGTTC GCAGTCCAGA
 551  ACTACCAAGT TCCTCTCTTG TCCGTGTACG TTCAAGCAGC TAATCTTCAC
 601  CTCAGCGTGC TTCGAGACGT TAGCGTGTTT GGGCAAAGGT GGGGATTCGA
 651  TGCTGCAACC ATCAATAGCC GTTACAACGA CCTTACTAGG CTGATTGGAA
 701  ACTACACCGA CCACGCTGTT CGTTGGTACA ACACTGGCTT GGAGCGTGTC
 751  TGGGGTCCTG ATTCTAGAGA TTGGATTAGA TACAACCAGT TCAGGAGAGA
 801  ATTGACCCTC ACAGTTTTGG ACATTGTGTC TCTCTTCCCG AACTATGACT
 851  CCAGAACCTA CCCTATCCGT ACAGTGTCCC AACTTACCAG AGAAATCTAT
 901  ACTAACCCAG TTCTTGAGAA CTTCGACGGT AGCTTCCGTG GTTCTGCCCA
 951  AGGTATCGAA GGCTCCATCA GGAGCCCACA CTTGATGGAC ATCTTGAACA
1001  GCATAACTAT CTACACCGAT GCTCACAGAG GAGAGTATTA CTGGTCTGGA
1051  CACCAGATCA TGGCCTCTCC AGTTGGATTC AGCGGGCCCG AGTTTACCTT
1101  TCCTCTCTAT GGAACTATGG GAAACGCCGC TCCACAACAA CGTATCGTTG
1151  CTCAACTAGG TCAGGGTGTC TACAGAACCT TGTCTTCCAC CTTGTACAGA
```

Fig. 3k (Cont...)

```
1201  AGACCCTTCA ATATCGGTAT CAACAACCAG CAACTTTCCG TTCTTGACGG
1251  AACAGAGTTC GCCTATGGAA CCTCTTCTAA CTTGCCATCC GCTGTTTACA
1301  GAAAGAGCGG AACCGTTGAT TCCTTGGACG AAATCCCACC ACAGAACAAC
1351  AATGTGCCAC CCAGGCAAGG ATTCTCCCAC AGGTTGAGCC ACGTGTCCAT
1401  GTTCCGTTCC GGATTCAGCA ACAGTTCCGT GAGCATCATC AGAGCTCCTA
1451  TGTTCTCTTG GATACACCGT AGTGCTGAGT TCAACAACAT CATCGCATCC
1501  GATAGTATTA CTCAAATCCC TGCAGTGAAG GAAACTTTC TCTTCAACGG
1551  TTCTGTCATT TCAGGACCAG GATTCACTGG TGGAGACCTC GTTAGACTCA
1601  ACAGCAGTGG AAATAACATT CAGAATAGAG GGTATATTGA AGTTCCAATT
1651  CACTTCCCAT CCACATCTAC CAGATATAGA GTTCGTGTGA GGTATGCTTC
1701  TGTGACCCCT ATTCACCTCA ACGTTAATTG GGGTAATTCA TCCATCTTCT
1751  CCAATACAGT TCCAGCTACA GCTACCTCCT TGGATAATCT CCAATCCAGC
1801  GATTTCGGTT ACTTTGAAAG TGCCAATGCT TTTACATCTT CACTCGGTAA
1851  CATCGTGGGT GTTAGAAACT TTAGTGGGAC TGCAGGAGTG ATTATCGACA
1901  GATTCGAGTT CATTCCAGTT ACTGCAACAC TCGAGGCTGA ATGAGAATTC
1951  ATGCTGATGT TTGTATGGAT CCTGAGCCCA TAGTGCGTAT CGTAGGTCGA
2001  AATGGTCTAT GTGTTGATGT TAGGGATGGA AGATTCCACA ACGGAAACGC
2051  AATACAGTTG TGGCCATGCA AGTCTAATAC AGATGCAAAT CAGCTCTGGA
2101  CTTTGAAAAG AGACAATACT ATTCGATCTA ATGGAAAGTG TTTAACTACT
2151  TACGGGTACA GTCCGGGAGT CTATGTGATG ATCTATGATT GCAATACTGC
2201  TGCAACTGAT GCCACCCGCT GGCAAATATG GATAATGGA ACCATCATAA
2251  ATCCCAGATC TAGTCTAGTT TTAGCAGCGA CATCAGGGAA CAGTGGTACC
2301  ACACTTACGG TGCAAACCAA CATTTATGCC GTTAGTCAAG GTTGGCTTCC
2351  TACTAATAAT ACACAACCTT TGTTACAAC CATTGTTGGG CTATATGGTC
2401  TAAGCTTGTC GAGAAGTACT AGAGGATCAT AATCAG
```

PESTICIDAL FUSIONS

TECHNICAL FIELD

The present invention relates to novel pesticidal fusion polypeptides having binding and toxic portions. It further relates to methods and materials for generating and employing such polypeptides, and also assays and kits for assaying the toxicity of polypeptides.

PRIOR ART

Toxins derived from *Bacillus thuringiensis* (Bt) are well known in the art to have insecticidal properties. In nature, large protoxin molecules (130–160 kDa) are solubilised in the alkaline environment of the insect midgut. The solubilised toxins are then proteolytically cleaved to smaller fragments (30–80 kDa). Following solubilisation and activation of delta endotoxin crystals, the toxin interacts with specific surface receptors of midgut cells and forms pores in the membrane. The ionic balance of the cells is disrupted and the cells lyse.

Of particular interest to users of Bt toxins are their host range, toxicity at low concentration, and the capacity of targeted insects to evolve resistance.

A variety of experiments have been reported which investigate these various issues, with a view to improving one or more of them with respect to the native toxin.

Thus it is generally accepted that presence of specific receptors on the apical membrane plays an important role in the specificity of Bt toxins (1). Under such circumstances, toxin potency may depend on receptor abundance and its affinity for the protein and also on the ability of the toxin to form pores. Insecticidal crystal proteins CryIA(a) and CryIA(c) are 82% homologous yet the latter protein has a 10-fold higher insecticidal activity towards *Heliothis virescens* and *Trichoplusia ni* than CryIA(a) (4). Homolog-scanning and reciprocal recombinations between these two genes indicated that amino acids 335–450 on CryIA(c) are associated with the activity against *T. ni* whereas amino acids 335–615 on the same toxin are required to exchange full *H. virescens* specificity (4).

In general, the specificity of an insecticidal protein is the result of several functions, including proteolytic processing by the insect midgut proteases, receptor binding and/or cytolytic functions (4). Results of terminal deletions of a lepidopteran specific insecticidal crystal protein indicated that deletions to the $10^{th}$ codon from the 51 end or the $645^{th}$ codon from the 3' end did not abolish toxicity (5).

Through site directed mutagenesis, Cry toxins have been tentatively determined to have three functional domains. Domain I is involved in toxin insertion into the membrane and affects ion channel function, domain II is involved in receptor binding and insertion into the membrane, and domain III is involved in ion channel function, receptor binding and insertion into the membrane (6).

Binding studies have been performed with two Bt delta endotoxins (Bt2, a 130 kDa recombinant crystalline protein from *B. thuringiensis* subsp. *berliner*) and Bt4412 (a 136 kDa crystalline protein form *B. thuringiensis* subsp. *thuringiensis*) on brush boarder membrane vesicles of the tobacco hornworm (*Manduca sexta*) and the cabbage butterfly (*Pieris brassicae*) (12). The Bt2 active protein (60 kDa) binds to and kills insects of both species whereas the Bt4412 active protein is highly toxic only to *M. sexta* larvae (12). It was revealed in this study that *P. brassicae* has two distinct binding sites for Bt2 and Bt4412 toxins because the two proteins competed negligibly for each others binding site (12).

A receptor for the CryIA(b) toxin was cloned from the midgut epithelial cells of the susceptible tobacco hornworm, *M. sexta* (13). The receptor, a 210 kDa membrane glycoprotein was determined to have 30–60% similarity and 20–40% identity to the caderin superfamily of proteins (13). Caderins are membrane glycoproteins and believed to mediate calcium-dependant cell aggregation and sorting (13). The proper function of the receptor was not elucidated. Suggestions though were that it may be involved in membrane transport, a function similar to that of the caderin-like human intestinal peptide transport protein, which channels peptide antibiotics through epithelial cells lining the small intestine (13). *B. thuringiensis* toxins are thought to act primarily at epithelial cells in the midgut of sensitive insects (13).

Another binding protein was purified from *M. sexta* and shown to be 120 kDa in size (14). The same protein, aminopeptidase N, was purified from *Lymantra dyspar* (the gypsy moth) brush boarder membrane vesicles (14). When tested against, CryIA(a), CryIA(b), CryIIA, CryIC, CryIIIA, CryIIB, CryID, CryIF, and CryIVD, aminopeptidase N purified from *L. dyspar* showed negligible binding activity (14). In contrast, aminopeptidase N purified from *M. sexta* was shown to bind CryIA(a), CryIA(b), and CryIA(c) with strong affinity (14). This disparity in the binding activity of aminopeptidase N, is unresolved. Instead it was speculated that either the protein differs according to the insect from which it was purified or that the differences reflect variations in the sensitivities of protocols employed (14). One crop pest, the diamondback moth (*Plutella xylostella*) has evolved resistance to Bt in open field populations, though laboratory selection experiments showed that many insects can develop resistance to Bt genes (17). It was shown that an autosomal recessive gene in *P. xylostella* confers extremely high resistance to four Bt toxins CryIA(a), CryIA (b), CryIA(c) and CryIF (16). This suggest that such a mutation conferring resistance to the four Bt toxins results in the disruption of binding to a single insect protein which acts as a receptor for all the four Bt toxins (16, 18). This suggests that resistance to even multiple-Bt containing plants is a real possibility.

WO 91/17254 (The regents of the university of California) discloses a method for improving the host range or toxicity of insecticidal toxins. Essentially the insecticidal protein were combined with the specific gut-epithelium-binding glycoprotein gp64 derived from the *Autographa califonica* multiple nuclear polyhedrosis virus (MNPV). This glyoprotein was said to interact with epithelial cell surface receptors, allowing concentration on, and entry into, midgut cells. In an alternative embodiment is was suggested that the Cyt A protein could be used to enhance toxicity. This protein was said to bind fatty acids in the lipid portion of cells, disrupting them through a detergent-like mode of action. The implications for resistance, if any, are not discussed.

The binding domains in natural Bt genes have also been swapped with other Bt genes to alter the toxicity of the proteins (see e.g. De Maagd et al (1996) Appl Env Microb 62 No 5:1537–1543). As described above, e.g. with reference to (16), this strategy may not give improved properties as regards possible resistance.

In the light of these observations it can be seen that novel toxin pesticidal materials, particularly those which offer an alternative approach or some advantage over those described above, would provide a contribution to the art.

DISCLOSURE OF THE INVENTION

The present inventors have synthesised fusion protein genes which express highly toxic fusion proteins. These proteins comprise a toxin domain fused to a heterologous binding domain which enhances the efficacy of the toxin portion. The binding domain is preferably one which can bind non-specifically to cell membranes without disrupting them—thereby allowing concentration and immobilisation of the toxin domain at its site of action without the requirement for particular receptors to be present. This has been exemplified using a Bt-derived portion and a carbohydrate binding portion, such as the galactose binding domain of the ricin toxin B chain gene.

The toxicity of the expression product has been demonstrated to be superior to be either of the constituent parts of the fusion protein, using a novel modified assay employing an insect cell-line and a pair of fluorescent dyes. The in vitro bioassay for the assessment of toxicity of the fusion gene products was developed and is based on the Ethidium homodimer 1 and Calcein AM. The two phlorophores have previously been used mainly in live/dead toxicity assays (39). These and other aspects of the invention will be described hereinafter.

Thus in a first aspect of the present invention there is disclosed a nucleic acid molecule encoding a pesticidal fusion polypeptide comprising (i) a toxin domain
(ii) a heterologous binding domain capable of binding non-specifically to a cell membrane without disrupting that membrane.

By 'pesticidal' is meant having toxicity against any one or more types of pest, particularly economically significant invertebrate pests including insects and other arthropods e.g. arachnida. Insects include all developmental stages of insect. Particular classes of insect of interest include Lepidoptera, Coleoptera, Culicidae, Simuliidae, Hymenoptera, Homoptera, Orthoptera and Diptera.

By 'fusion polypeptide' is meant a polypeptide comprising two or more components which are heterologous to each other i.e. not part of a naturally occurring single polypeptide chain. Optionally a linker region may be included which may facilitate the folding of the domains into their natural conformation by reducing steric hindrance between the domains.

By 'toxin' is meant a material which is toxic to pests, preferably at a quantity capable of being ingested by a pest. The toxin portion of the fusion protein may be synthetic or from a natural source e.g. prokaryotes, eukaryotes (including fungi, plants and animals). Particularly envisaged is use of proven protein toxins (such as the Bt toxins, or plant defensive allochemics e.g. protease inhibitors such as that from cowpea or soybean) or portions thereof. Preferably these will be pesticidal but be non-toxic to humans and animals. The toxin will preferably be one which has its actual site of action at the cell membrane.

The Bt toxins discussed above are particularly effective as sources of the toxin component. In the most preferred forms of the first aspect of the invention, the toxin is derived from a Bt cry polypeptide. Thus in one embodiment of this aspect the toxin is Bt cryIA(b) or (c).

The 'binding' domain of the fusion polypeptide can bind non-specifically to a cell membrane without disrupting it, and is thus non-toxic per se.

'Non-specifically' in this context means not requiring a particular, specific, receptor. This has the advantage that it reduces the probability that the pest will be able to develop resistance to the fusion through a mutation in the nucleic acid sequence encoding a toxin receptor, as is thought to be the case with some Bt resistance (see refs 16,17,18). It provides an alternative approach to physical methods which may be used to minimise the likelihood of resistance developing i.e. mixing Bt-transformed plants with non-transformed plants during sowing to minimise selective pressure.

The 'binding' domain is non-toxic per se i.e. although it may enhance the toxicity of the toxin domain, it does not itself cause significant, or more preferably any, disruption to the cell membrane either when used alone in the fusion protein. Thus the binding portion effectively serves to allow the toxin to exert its effect, but preferably does not alter the mode of action of the toxin mechanism, thereby providing a more predictable specificity and response. This is particularly useful in embodiments wherein the fusion protein may enter the animal food chain, and where the toxin has been carefully selected to be non-toxic to animals.

Preferably the binding domain binds carbohydrate, which is present on the extracellular side of all eucaryotic cell membrane in the form of glycolipids and glycoproteins. The binding domain will thus serve to anchor the toxin at a site of action in wide variety of cells.

Preferably the cells form part of the pest gut epithelia.

It is preferred that the toxin actually be immobilised at the site of action, but even if actual (irreversible) immobilisation does not occur, the use of the heterologous binding domain will still act to increase the effective concentration of the toxin at its site of action at the cell membrane.

In one embodiment of this aspect the binding domain consists of all or part of a lectin. Lectins are well known in the art for their ability to bind tightly to carbohydrate, different lectins generally having particular affinities for different sugar residues. Particularly desirable are domains with galactose or galactosyl affinity, which would allow very widespread binding within the target pest class.

Preferably the lectin is a type two ribosome inactivating protein, and the (non-toxic) B chain is used. Examples of this type include:

(a) *Abrus precatorius* (Abrin)
(b) *Viscum album* (Viscumin)
(c) *Adenia digitata* (Modeccin)
(d) *Adenia volkensii* (Volkensin)

A table listing the origin and the properties of the four examples above is given (Stirpe, et al., 1992. Ribosome-inactivating proteins from plants: present status and future prospects. Bio/Technology, vol. 10, 405–412; Barbieri, et al., 1993. Ribosome-inactivating proteins from plants. Biochemica et Biophysica Acta, vol. 1154, 237–282).

Most preferably the ricin toxin B chain gene, derived from the ricin toxin, is used in the nucleic acid. Ricin is a toxic glycoprotein comprising two polypeptide chains, A and B, linked by a disulfide bond (32).

The binding of the B-chain to galactosyl terminated residues on cell surfaces is accomplished by two galactose binding domains located at either end of the peptide (34). Each of the two binding sites is capable of binding galactose and more complex sugars in the absence of the other site with no significant decrease in affinity for the ligand (35).

It has been shown that double lectin site ricin B chain mutants expressed in insect cells have residual galactose binding: evidence for more than two lectin sites on the ricin toxin B chain. Bioconjugate, Chem. vol. 7, 651–658; Ferrini, et al., 1995. Expression of functional ricin B chain using the baculovirus system. Eur. J. Biochem. vol. 233, 772–777). This suggests that other cell-surface binding sites may exist. One possibility is that mannose side chains on the ricin B chain itself interact with mannose receptors on the cell surface (see Newton et al (1992) J Biol Chem 267(17): 11917–11922; Frankel et al (1997) Carbohydrate Research 300,3:251–258).

The binding of its B-chain to the cell surface, for instance to a glycoconjugate having non-reducing terminal galactose residue, causes or facilitates the internalisation of ricin into the cell. Internalisation may be via endocytic uptake in both coated and uncoated pits (see Frankel et al (1996) Protein Engineering 9, 4:371–379; Magnusson and Berg (1993) Biochem J 291: 749–755). Following routing and release of the free A-chain into the cytosol, cellular protein synthesis in eukaryotic cells is inhibited through the cleavage of a single adenine residue from eucaryotic 28 S RNA in the 60S ribosomal subunit (33). Several recent reports support a broad role for ricin toxin B chain; the polypeptide is thought not only to interact with cell surface galactose residues, but it may also be involved in the intracellular trafficking of the ricin toxin (44). Many receptors that recycle through endosomal vesicles to the cell surface pass through the trans-Golgi network. Within cells, the Golgi has the densest concentration of ricin binding sites, probably reflecting the concentration of galactosyltransferases in this cellular compartment (45). Ricin toxin entering cells by interacting with galactose-terminated receptors has been observed to concentrate in the Golgi region (45).

Although recombinant B chain lectin derivatives have been prepared in the past, this has generally been for therapeutic applications, in order to enhance the toxicity of the A chain. Thus it has been observed in many experiments that immunotoxins constructed with the ricin toxin B and A chain together are consistently more toxic than those constructed with, for example, ricin toxin A chain alone (see e.g. Vitetta, et al., 1991 Sem. Cell Biol. vol. 2, 47–58; Timar, et al., 1991 Br. J. Cancer, vol. 64, 655–662; Embleton, et al., 1991 Br. J. Cancer vol. 63, 670–674).

Thus a second aspect of the invention is a nucleic acid molecule comprising
(i) a sequence encoding all or part of Bt cry polypeptide, and
(ii) a sequence encoding all or part of a lectin.

Nucleic acid molecules and their encoded polypeptide products according to the present invention may be provided isolated and/or purified from their natural environment, in substantially pure or homogeneous form, or free or substantially free of nucleic acid or genes of the species of interest or origin other than the sequence encoding a polypeptide with the required function.

Nucleic acid according to the present invention may include cDNA, RNA, genomic DNA and may be wholly or partially synthetic.

The term "isolated" encompasses all these possibilities. Where a DNA sequence is specified, e.g. with reference to Seq ID Nos 1–11 of FIG. 3(a)–(k), unless context requires otherwise the RNA equivalent, with U substituted for T where it occurs, is encompassed, as are degeneratively equivalent and complementary sequences.

Preferably the Bt cry toxin-encoding portion of the nucleic acid molecule comprises all or part of Seq ID No 1 (CryIA(b)) or Seq ID No 2 (CryIA(c)).

Preferably the lectin-encoding portion of the nucleic acid molecule comprises all or part of Seq ID No 3 (RTB1), Seq ID No 4 (RTB2) or Seq ID No 5 (RTB3); these were derived from ricin toxin B chain as described below, but included mutations to introduce restriction sites.

Preferably the nucleic acid molecule comprises the CryIA-RTB combination shown in any one of Seq ID No 6 (CryIA(b)-RTB1); Seq ID No 7 (CryIA(b)-RTB2); Seq ID No 8 (CryIA(b)-RTB3); Seq ID No 9 (CryIA(c)-RTB1); Seq ID No 10 (CryIA(c)-RTB2); or Seq ID No 11 (CryIA(c)-RTB3).

It should be stressed that the invention also extends to nucleic acids encoding variants of naturally occurring toxin and binding molecules, which may for instance be mutants or other derivatives of such molecules. In particular nucleic acids having modified sequences based on Seq ID Nos 1 to 11 are included.

In each case the variant encodes a toxin or binding product either of which is homologous to a naturally occurring sequence (e.g. Bt Cry or a lectin) and retains the appropriate functional characteristic of that product (e.g. toxicity or the ability to bind glycosylation respectively).

Similarity or homology may be as defined and determined by the TBLASTN program, of Altschul et al. (1990) J. Mol. Biol. 215: 403–10, which is in standard use in the art, or, and this may be preferred, the standard program BestFit, which is part of the Wisconsin Package, Version 8, September 1994, (Genetics Computer Group, 575 Science Drive, Madison, Wis., USA, Wisconsin 53711).

Homology may be at the nucleotide sequence and/or amino acid sequence level. Preferably, the nucleic acid and/or amino acid sequence shares about 50%, or 60%, or 70%, or 80% homology, most preferably at least about 90%, 95%, 96%, 97%, 98% or 99% of the sequence upon which the variant is based (e.g. the natural sequence, or any one Seq ID Nos 1 to 11). Homology may be over the full-length of the relevant sequence or may more preferably be over a contiguous sequence of about or greater than about 20, 25, 30, 33, 40, 50, 67, 133, 167, 200 or more amino acids (or codons) compared with the relevant amino acid sequence or nucleotide sequence as the case may be.

Thus a variant sequence in accordance with the present invention may encode, for instance within the (hybrid sequences, Seq ID Nos 6 to 11) a single amino acid change with respect to those sequences, or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence encoded by the depicted sequences, an encoded variant amino acid sequence may include additional amino acids at the C-terminus and/or N-terminus. Naturally, changes to the nucleic acid which make no difference to the encoded amino acid sequence (i.e. 'degeneratively equivalent') are included.

Homology may be assessed using hybridization technology (52) for instance using a hybridization solutions comprising: 5×SSC (wherein 'SSC'=0.15 M sodium chloride; 0.15 M sodium citrate; pH 7), 5× Denhardt's reagent, 0.5–1.0% SDS, 100 µg/ml denatured, fragmented salmon sperm DNA, 0.05% sodium pyrophosphate and up to 50% formamide.

One common formula for calculating the stringency conditions required to achieve hybridization between nucleic acid molecules of a specified sequence homology is (52): $T_m=81.5°$ C.$+16.6$ Log [Na+]$+0.41$ (% G+C)$-0.63$ (% formamide)$-600$/#bp in duplex As an illustration of the above formula, using [Na+]= [0.368] and 50-% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

Particularly useful for certain applications e.g. expression in plants, may be alteration of codon usage (i.e. degeneratively neutral mutation) in order to assist expression. For instance, the AU/GC ratio for Cry genes deviates significantly from values found for plant coding regions and well expressed reporter genes like nptII, bar, gus and cat (24). A plant coding region typically has an AU content of about 40–50%, whereas the CryI coding regions have an AU content of 60–64%, exceeding in some regions 70% (24). Also, the codon usage of the Cry-coding sequence is very unlike the preferred plant codon usage (25). There are clusters of unfavourable codons at several sites. Altering the codon usage may enhance efficient translation and elongation thus rendering the mRNA more stable to cytoplasmic Rnase activities (23, 26).

The mutants as described herein will have the enhanced binding properties discussed above.

One possible mode of analysis for mutants or other derivatives is by transformation to assess function on introduction into a host cell capable of expressing the nucleic acid of the invention, and the subsequent comparison of the viability of that cell with cells transformed with other nucleic acids. Methodology for such transformation and analysis, exemplified using SF21 insect cells, is described in more detail below. Another method comprises the use of transgenic plants expressing the mutant or derivative.

Methods for producing such a mutant or derivatives as disclosed above embrace any method familiar to those skilled in the art.

Thus a further aspect is a method of producing a nucleic acid encoding a pesticidal fusion polypeptide comprising the step of combining a nucleic acid encoding a toxin with a nucleic acid encoding a heterologous binding domain, wherein said binding domain is capable of binding non-specifically to a cell membrane without disrupting it.

Optionally this method may include, or be preceded by, steps whereby changes to the sequence of the toxin or binding domains are made such as to produce a mutant or derivative, which may be by way of addition, insertion, deletion or substitution of one or more nucleotides in the nucleic acid, leading to the addition, insertion, deletion or substitution of one or more amino acids in the encoded polypeptide.

Changes may be desirable for a number of reasons, including introducing or removing the following features: restriction endonuclease sequences; other sites which are required for post translation modification; cleavage sites in the encoded polypeptide; motifs in the encoded polypeptide for glycosylation, lipoylation etc. Leader or other targeting sequences may be added to the expressed protein to determine its location following expression. All of these may assist in efficiently cloning and expressing an active polypeptide in recombinant form (as described below).

Other desirable mutation may be random or site directed mutagenesis in order to alter the activity (e.g. specificity) or the affinity or stability of the encoded polypeptide.

As is well-understood, polypeptide homology is judged in terms of amino acid similarity or identity (in this case with respect to the altered toxin domain and/or binding domain).

Similarity allows for conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Also included are homologs having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide e.g. yet further improved toxicity or host-range.

In one aspect of the present invention, the nucleic acid described above is in the form of a recombinant and preferably replicable vector.

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Particularly favoured for some applications are BAC or BiBAC vectors.

Specifically included are shuttle vectors by which is meant a DNA vehicle capable, naturally or by design, of replication in two different host organisms, which may be selected from actinomycetes and related species, bacteria and eucaryotic (e.g. higher plant, mammalian, yeast or fungal cells).

A vector including nucleic acid according to the present invention need not include a promoter or other regulatory sequence, particularly if the vector is to be used to introduce the nucleic acid into cells for recombination into the genome.

Preferably, however, the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

Thus this aspect of the invention provides a gene construct, preferably a replicable vector, comprising a promoter operatively linked to a nucleotide sequence provided by the present invention as described above, such as the Seq ID no 9, 10 or 11.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press.

Many known techniques and protocols for manipulation of nucleic acid, for example in preparation of nucleic acid constructs, mutagenesis (see above), sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711–8721 (1984)) and Guerineau and Mullineaux (1993) (Plant transformation and expression vectors. In: Plant Molecular Biology Labfax (Croy RRD ed) Oxford, BIOS Scientific Publishers, pp 121–148).

Particular of interest in the present context are insect-cell vectors (e.g. based on baculovirus) and plant vectors.

Suitable promoters which operate in plants include the Cauliflower Mosaic Virus 35S (CaMV 35S) gene promoter that is expressed at a high level in virtually all plant tissues (Benfey et al, 1990a and 1990b); the cauliflower meri 5 promoter that is expressed in the vegetative apical meristem as well as several well localised positions in the plant body, e.g. inner phloem, flower primordial branching points in root and shoot (Medford, 1992; Medford et al, 1991) and the *Arabidopsis thaliana* LEAFY promoter that is expressed very early in flower development (Weigel et al, 1992). Other promoters include the rice actin promoter.

In one embodiment of this aspect of the present invention provides a gene construct, preferably a replicable vector, comprising an inducible promoter operatively linked to a nucleotide sequence provided by the present invention.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

A suitable inducible promoter may be the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues. Other promoters include the potatin promoter (tubers) and the ubiquitin promoter (wheat embryos).

The promoter may include one or more sequence motifs or elements conferring developmental and/or tissue-specific regulatory control of expression.

Particularly advantageous in the present context may be an inducible promoter which is switched on in response to elicitors, or other plant signals which are triggered during predation. This system may assist in reducing the likelihood of resistance in feeding-pests over long periods owing to selection pressure which is brought to bear by constitutively toxic plants.

The present invention also provides methods comprising introduction of such constructs into a plant cell and/or induction of expression of a construct within a plant cell, by application of a suitable stimulus, an effective exogenous inducer.

The vectors described above may be introduced into hosts by any appropriate method e.g. conjugation, mobilisation, transformation, transfection, transduction or electroporation, as described in further detail below.

In a further aspect of the invention, there is disclosed a host cell containing nucleic acid or a vector according to the present invention, especially a plant, insect or a microbial cell.

Plants cells transformed with the DNA segment containing the sequence may be produced by standard techniques which are well known to those skilled in the art.

Thus DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser) other forms of direct DNA uptake (DE 4005152, WO 9012096, U.S. Pat. No. 4,684, 611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1–11.

*Agrobacterium* transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep.* 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994)

*Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, *Agrobacterium* mediated transformation is now emerging also as an highly efficient alternative transformation method in monocots (Hiei et al. (1994) *The Plant Journal* 6, 271–282).

Microprojectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

If desired, selectable genetic markers may be used consisting of chimeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

A number of plants that have been transformed with Bt genes have been reported in the art. In particular, transgenic maize resistant to extremely high and repeated infestations with the European corn borer were obtained using a synthetic version of CryIA(b) (27). Transformation with the native Bt gene had failed to effect production of detectable levels of protein whereas raising the G-C content from 38% to 65% produced a gene which is highly expressed in maize (27). This CryIA(b) gene has about 65% homology at the nucleotide level with the native gene and is designed to resemble a maize gene in terms of codon usage (27). Thus in those aspects of the present invention in which the pesticidal-fusion genes are introduced into plants for expression, it may be desirable to correspondingly alter the codon usage as described in (27) in order to increase polypeptide yield.

Thus a further aspect of the present invention provides a method of transforming a plant cell involving introduction of a vector of the present invention into a plant cell and causing or allowing recombination between the vector and the plant cell genome to introduce the sequence of nucleotides into the genome.

The invention further encompasses a host cell transformed with nucleic acid or a vector according to the present invention, especially a plant or a microbial cell. In the transgenic plant cell (i.e. transgenic for the nucleic acid in question) the transgene may be on an extra-genomic vector or incorporated, preferably stably, into the genome. There may be more than one nucleotide sequence per haploid genome.

Thus in one embodiment of this aspect of the invention there is provided a plant cell having incorporated into its genome nucleic acid of the present invention, under operative control of a regulatory sequence for control of expression. The coding sequence may be operably linked to one or more regulatory sequences which may be heterologous or foreign to the pesticidal fusion polypeptide gene i.e. not naturally associated with either part of the gene for its expression. The nucleic acid according to the invention may be placed under the control of an externally inducible gene promoter to place expression under the control of the user.

Generally speaking, following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

In addition to the regenerated plant, the present invention embraces all of the following: a clone of such a plant, seed, selfed or hybrid progeny and descendants (e.g. F1 and F2 descendants) and any part of any of these, such as cuttings, seed.

The invention also provides a plant propagule from such a plant, that is any part which may be used in reproduction or propagation, sexual or asexual, including cuttings, seed and so on.

A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

The invention further provides a method of influencing or affecting the toxicity of a plant to a pest including causing or allowing expression of a pesticidal fusion polypeptide gene as discussed above within cells of the plant.

The invention further provides a method of including expression from a nucleic acid of the present invention (e.g. as shown in FIG. 3, or a mutant, allele or derivative of that sequence) within cells of a plant (thereby producing the encoded polypeptide), following an earlier step of introduction of the nucleic acid into a cell of the plant or an ancestor thereof. Such methods will influence or affect the resistance which the plant has to the particular pest. Preferably the plant will be immune to the pest i.e. the pest will not consume or injure the plant under any known conditions. Alternatively resistance may be high or low (i.e. damage is below average) with respect to untransformed plants.

Naturally the present invention also encompasses the expression product of any of the nucleic acid sequences disclosed and methods of making the expression product by expression from encoding nucleic acid therefore under suitable conditions, which may be in suitable host cells.

Following expression, the product may be isolated from the expression system (e.g. microbial) and may be used as desired, for instance in formulation of a composition including at least one additional component (e.g. carrier liquid). Such insecticidal compositions may be employed, for instance as sprays, particularly in situations which are analogous to those in which the toxin component of the fusion protein may have been employed previously.

Thus a plant or other commodity susceptible to attack by pests treated with such a composition also forms part of the present of the present invention.

Alternatively the polypeptide product may perform its function in vivo, or in situ as described above.

Thus the invention also embraces a method of controlling pests comprising the use of a polypeptide of the present invention (or composition, or host cell comprising it), particularly a method of killing pests comprising the administration, or causing or allowing the ingestion, of the polypeptide (or composition, or host cell comprising it) to the pests.

The purified polypeptides of the invention, may be used to raise antibodies employing techniques which are standard in the art. Antibodies and polypeptides comprising antigen-binding fragments of antibodies may be used e.g. in assays for the polypeptide, or for labelling it.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest.

For instance, Western blotting techniques or immunoprecipitation may be used (Armitage et al, 1992, Nature 357: 80–82). Antibodies may be polyclonal or monoclonal. Antibodies may be modified in a number of ways. Indeed the term "antibody" should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of Chimaeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the Vl and VH domains of a single antibody; (iv) the dAb fragment (Ward, E. S. et al., Nature 341, 544–546 (1989) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1988; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P Holliger et al Proc. Natl. Acad. Sci. USA 90 6444–6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

In a yet further aspect of the present invention there is disclosed a method of assessing the toxicity of a polypeptide to a particular species comprising:
(i) introducing a nucleic acid encoding said polypeptide into a host cell from that species,
(ii) causing or allowing the nucleic acid to be expressed in a host cell from that species,
(iii) observing the viability of the cell and correlating the results of the observation with the toxicity of the polypeptide.

The introduction and expression of the toxin can be carried out as described above. Preferably a well characterised promoter is used in order to minimise any variation in transcription. The viability can be assessed by any method known in the art, possibly only by visual observation alone, or using EM observation. However, in preferred embodiments, the method comprises use of an assay which assesses esterase activity or membrane integrity, for instance an assay based on the Ethidium homodimer 1, Calcein AM or trypan blue (see Molecular Probes, product Information sheet, Live/dead/cytotoxicity kit, L-3224). Ethidium homodimer 1 and Calcein AM assay different aspects of cell viability—plasma membrane integrity and intracellular esterase activity respectively (40, 41).

Although these phlorophores have previously been used in live/dead assays (39), they have not been used in relation to a specifically introduced toxin-encoding nucleic acid.

Membrane integrity assays may be particularly useful for assaying toxins (e.g. Bt cry-based toxins) which are thought to act on membranes.

The assay format of the present invention has a number of useful characteristics—in particular the cytotoxic agent is not externally applied. This eliminates the need for measurement of the cytotoxic agent and its purification.

Thus in the present context the polypeptide may be the pesticidal polypeptide described above. The host cell will be from an appropriate pest e.g. an insect cell.

Preferably the result of the viability assessment is compared with that from a control cell in which the toxin has not been expressed, but optionally in which other heterologous nucleic acids have been introduced. Such a comparison will improve the confidence with which a correlation can be made.

Baculoviruses are particularly effective vectors for use in this method because protein synthesis using these vectors is temporal (Miller (1988) Ann Rev Microbiol 42:177–199). Other things being equal the protein concentration in the control and experimental cells will increase steadily with concomitant toxic effect, the severity of which will be determined by the $LC_{50}$ of the protein.

The invention will now be further illustrated with reference to the following non-limiting Figures and Examples. Other embodiments falling within the scope of the invention will occur to those skilled in the art in the light of these.

FIGURES

FIG. 1—Constructs expressed in Sf21 cells and transgenic rice plants. (A) Site-directed mutagenesis of the ricin toxin B-chain (RTB) to derive 3' terminal fragments spanning the galactose-binding domains (green boxes). Mismatched oligonucleotides LF1, LB1, LB2 and LB3 were used to introduce novel EcoRI (LF1) and HindIII (LB1, LB2, and LB3) sites. Three RTB fragments were obtained and called RTB1, RTB2 and RTB3. (B) Schematic diagrams of the control and fusion cassettes. Bt cry1Ab and cry1Ac sequences are shown as orange boxes, and RTB fragments as thick lines. Constructs pB and pC were Bt controls, constructs pR1, pR2 and pR3 were RTB controls, and pBR1, pBR2, pBR3, pCR1, pCR2 and pCR3 were fusion constructs. Restriction sites are shown for pBR1 only but apply to all constructs. Sites are abbreviated as follows: B=BamHI, Ec=EcoRI, Eh=EheI, H=HindIII. (C) For expression in transgenic plants, the 11 constructs were cloned in the vector pAC76 containing the maize ubiquitin-1 promoter and first intron, and the nos terminator. Restriction sites are abbreviated as follows: Eh=EheI, H HindIII, S=SmaI.

Figure 2:
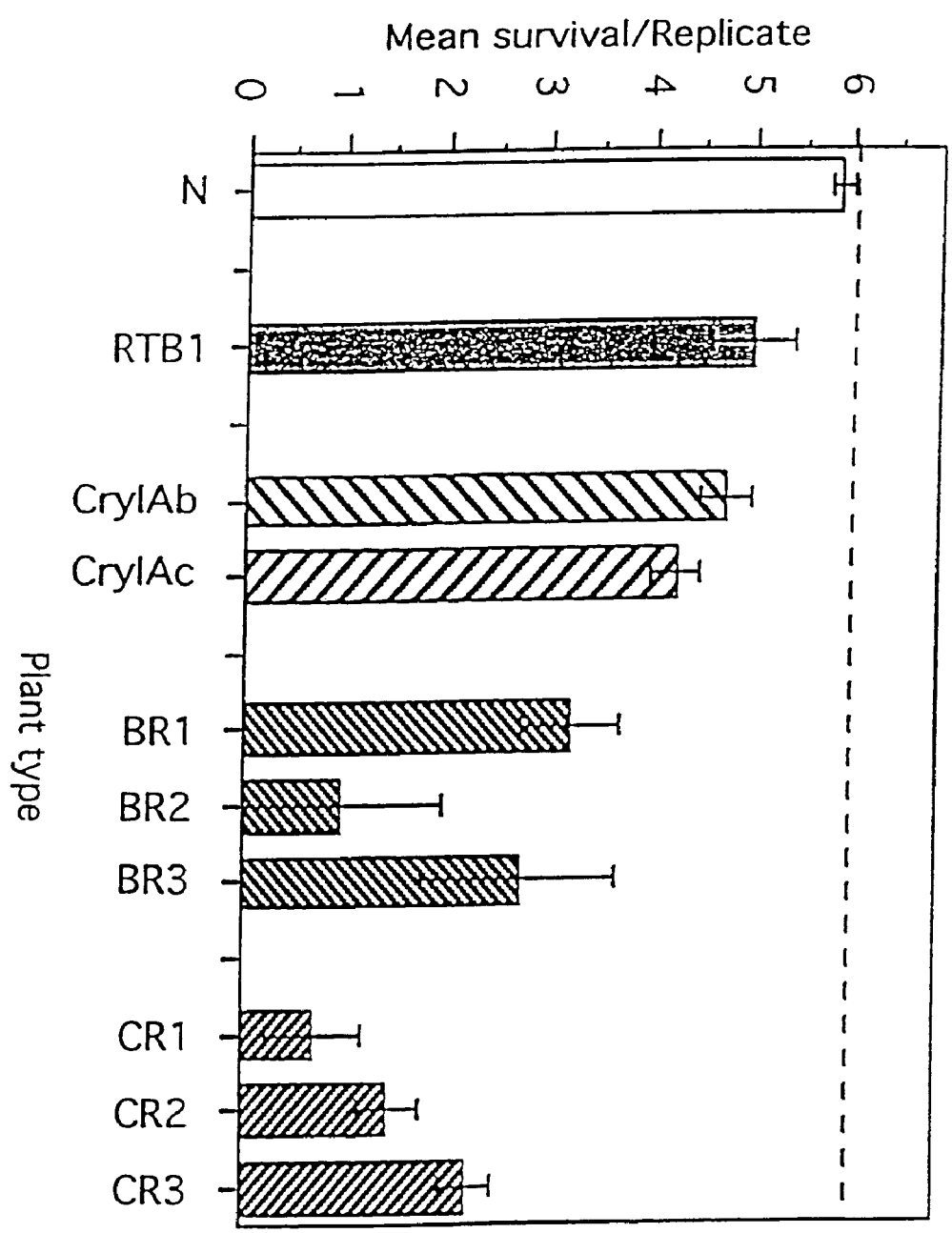

FIG. 2—Survival, growth and development of stem borer larvae feeding on transgenic rice stems and controls. Graph showing mean insect survival +SE after 4 days (initial inoculum of six neonate larvae). Each value represents the mean of four replicate bioassays, except the control, which represents six replicate bioassays.

Figure 3G:
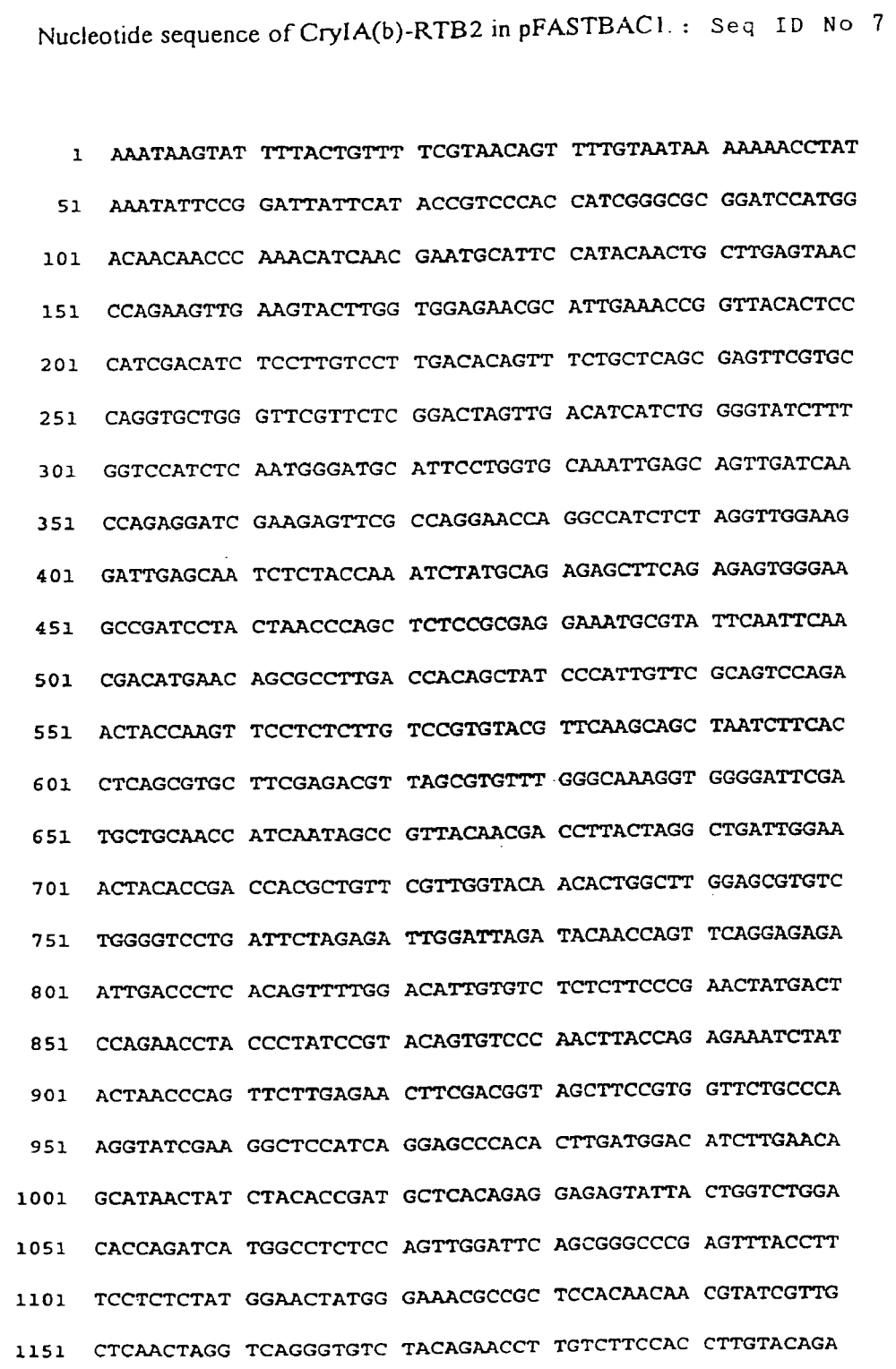

FIG. 3($a$) to ($k$)—This shows the nucleotide sequences of CryIA (b&c), the ricin toxin B chain gene fragments and the fusion genes cloned in pFASTBAC1 under the control of the polyhedrin promoter. The sequences in FIGS. 3($a$)–($k$) are labeled Seq ID Nos 1–11, respectively. All sequence read 5'-3' direction. The codon ATG starting at nucleotide 97 is the translation initiation site for the genes CryIA(b&c) and all the fusion genes. For the ricin toxin B chain fragments the codon ATG starting at nucleotide position 125 serve as the translation initiation site. All the genes are terminated by the SV40 polyadenylation sequence. The stop codons TAG and TAA are employed and their positions (if sequences are read in the 5'–3' direction) vary with the size of each gene. If the sequences are read from the 3'–5' direction the two codons TAG and TAA are located at nucleotide positions 17 and 7 respectively.

EXAMPLES

Materials. All restriction endonucleases, $T_4$ ligase and all restriction enzymes were obtained from Boehringer Mannheim (U.K.). The QUIAGEN plasmid kit and the QUI-Aquick gel extraction kit were acquired from QUIAGEN. The pGEM-T cloning vector was purchased from Promega (U.K.). The Ethidium homodimer 1 and Calcein AM were purchased from Molecular probes Europe BV (Nerherlands). The pFASTBAC1 baculovirus transfer vector, the TC-100 insect cell culture dishes and media, fetal calf serum, cellfectin and the DH10BAC competent cells were purchased from GIBCO BRL (U.K.). The ricin toxin B chain gene (plasmid pWBT) and the anti-ricin toxin B chain antibodies used in this research were kindly given by Dr. L. Roberts of Warwick University. The plasmids pUBB and pUBC containing the CryIA(b) and CryIA(c) genes were kindly given by Dr. I. Altosaar of the University of Ottawa, Canada and were as described (Sardana, et. al., 1996). All primers used were synthesised at Genosys Biotechnologies (England).

Example 1

Preparation of Toxin Gene

Site directed mutagenesis of ricin toxin B chain gene. Four mutagenic oligonucleotides were used in PCR reactions to create an EcoRI and a HindIII restriction site at selected positions along the ricin toxin B chain gene in the plasmid pWT (Wales et. al., 1991)—these are shown in FIG. 1A. The five mutagenic oligonucleotides (mutated bases underlined) were:

LF1=5' CAACAACAAAG<u>GAA</u>TT<u>C</u>ATGCTGATG 3' (Seq ID No 12)

LB1=5' GGACACACACACTGCAAG<u>CTT</u>GTAATC 3' (Seq ID No 13)

LB2=5' CGGATCCGA<u>AA</u>AGC<u>T</u>TCACATCTAACAC 3' (Seq ID No 14)

LB3=5' GCTTGCAAGC<u>TT</u>AGACCATATAGCCC 3' (Seq ID No 15)

PCR mutagenesis was carried out in a 50 ml total volume containing 1×PCR buffer (Boehringer Mannheim), 200 mM each dNTP, 15 mM $MgCl_2$, 300 nM each primer, 2.6 units enzyme mix (Boehringer Mannheim) and 70 ng pBWT plasmid DNA. After an initial denaturation step at 94° C. for 2 min, 10 fixed amplification cycles were carried out (94° C., 15 s; 65° C., 30 s; 72° C., 1 min) followed by another progressively lengthening 20 cycles (94° C., 15 s; 65° C., 30 s; 72° C., 1 min; elongation increasing by 5 s each cycle). A final extension step was carried out at 72° C. for 7 min. PCR products were sized by 0.8% agarose gel electrophoresis, purified (QIA-quick gel extraction kit, Qiagen) and subcloned in the vector pGEM-T (Promega). Insert size and orientation was confirmed by digestion with EcoRI and HindIII.

Sequencing, to confirm the original RTB sequence, was carried out using M13/pUC19 primers (Gibco BRL) and the BIG DYE sequencing kit (Boehringer Mannheim). Cycling sequencing was carried out using the PTC-200 Peltier thermal cycler (M.J. Research Inc.).

Example 2

Preparation of Fusion in Baculovirus Vector

Overview of Baculovirus System

The insect baculoviruses *Autographa californica* (Ac) and *Bombyx mori* nuclear polyhedrosis viruses (MNPV) had previously been shown to be versatile high level expression vectors of heterologous proteins (6, 7, 13, 17). This is mainly due to the unique nature of the baculovirus replication cycle, which involves the sequential expression of virus encoded genes in four, temporary distinct phases (2, 7, 10, 18). The first three stages result in the production of infectious virus particles which invade other cells and therefore disseminate infection. In the final, very late phase of gene expression, starting at about 18 hours post infection, virus particles are occluded into crystalline proteinacious structures called polyhedra (7). The polyhedrin gene is dispensable for the production of virus particles and can be replaced with foreign coding sequences (7, 27). Because the polyhedrin gene is expressed in the late phase of gene expression it can be replaced with sequences coding for toxic proteins without affecting viral infectivity.

Several insecticidal crystal toxins have been shown to be expressible in baculovirus infected insect cells. The complete insecticidal crystal protein gene cryIA(b) was cloned into AcNPV, replacing the polyhedrin gene (8). A full length and a truncated bacterial CryIVD mosquitocidal protein were also successfully expressed in lepidopteran cells using the baculovirus vector (11).

Cloning into pFASTBAC1 baculovirus transfer vector.

The cry1Ab and cry1Ac genes were excised from source plasmids (pUBB and pUBC (46) by digestion with BamHI and EcoRI, and subcloned in the baculovirus transfer vector pFASTBAC Hb (Gibco). The recombinant plasmids were digested with EcoRI and HindIII allowing directional subcloning of the ricin gene fragments. Six intermediate pFASTBAC Hb fusion constructs were generated, representing the two Bt genes each fused to one of the three RTB fragments. These were digested with Eco47III and EcoRI (cry1Ab) or EcoRI and Xho I (cry1Ac), and the termini were polished using mung bean nuclease, thus bringing the Bt and RTB coding regions in-frame upon re-ligation (FIG. 1). The recombinant plasmids were then digested with StuI and HindIII, allowing directional subcloning of the fusion constructs in the similarly digested vector pFASTBAC1, whose polylinker is flanked with Tn7 attachment sites. The pFASTBAC1 vector was also digested separately with BamHI and EcoRI or with EcoRI and HindIII to allow subcloning of the two unmodified Bt genes and the RTB fragments, respectively, as controls.

Site specific transposition.

Recombinant pFASTBAC1 transfer vectors were transformed into competent *Escherichia coli* cells of strain DH10BAC (Gibco BRL). These cells contain a modified baculovirus genome carrying a Tn7 attachment site, and a plasmid providing Tn7 transposase, allowing site-specific transposition of the cassettes cloned in pFASTBAC1 into the baculovirus genome. White colonies were isolated and from them high molecular weight DNA was purified as outlined (37).

Recombinant bacmids were confirmed using PCR and the M13/PUC19 primers. Five microliters of a 10× PCR buffer, one microliter of 10× dNTP mix, 1.25 μl of a 10 uM stock of each primer, 1.5 μl of a 50 mM $MgCl_2$, 2.5 μl of a 1% solution of the detergent W-1, one microliter of template DNA and 2.5 units of Taq polymerase were used in 50 ul PCR reactions. After incubation at 93° C. for three minutes 35 cycles of PCR were performed as follows: 94° C. for 45 seconds, 55° C. for 45 seconds and 72° C. for five minutes (37). Ten microliters of the PCR reactions were electrophoresed on a 0.8% agarose gel.

Results of Vector Construction

Three terminal deletions of the ricin toxin B-chain gene were obtained. Digestion of the resultant pGEM-T recombinant vectors with the restriction enzymes EcoRI and HindIII yielded the expected three ricin toxin B chain gene deletions RTB1, RTB2 and RTB3. For RTB3 (480 bp, AA1–AA139) primers LF1xLB3 were used; RTB2 (739 bp, AA1–AA236) primers LF1xLB2 were used); and LB1 (841 bp, AA1–AA262) primers LF1xLB1 were used.

The three ricin toxin B chain fragments were then fused with the two Bt genes (using the EcoRI site of each gene) to achieve six different translation fusion proteins. The six translation fusion protein genes were confirmed through restriction enzyme digestion (results not shown).

The fusion genes were then transposed into the baculovirus genome under the control of the polyhedrin promoter. Success of site specific transposition was confirmed by PCR using the M13/PUC primers. The primers are directed towards the Tn7 attachment site of the baculovirus genome. A PCR reaction on this region alone (without any construct) yields a 300 base pair fragment. If this region is transposed with a non recombinant pFASTBAC1 DNA, a PCR on this region using the M13/PUC19 primers yields a DNA fragment of 2 300 base pairs. The results of the PCR (not shown) confirm successful transposition of the entire translation fusion protein gene expression cassettes as indicated by the corresponding increase of size in excess of 2 300 base pairs.

These recombinant baculoviruses were then transfected into Sf21 insect cells. High molecular weight DNA extracted from infected insect cells also confirmed (through PCR using the M13/PUC primers) the successful infection of the insect cells (results not shown).

Example 3

Production of Host Cells Expressing Pesticidal Fusion Polypeptide

Transfection of Sf21 insect cells with recombinant bacmid DNA. One million Sf21 insect cells were seeded in a 35 mm cell culture plate overnight in 2 mls of TC-100 media supplemented with 10% fetal calf serum. The cells were washed two times with serum and antibiotic free media and overlain with one ml of the transfection mix (5 microliters recombinant bacmid DNA, 800 μl serum and antibiotic free TC-100 media and six microliters cellfectin) for five hours (37). After removal of the transfection mix the cells were then covered with complete TC-100 media (supplemented with 10% fetal calf serum) for 48 hours. The virus was harvested (first inoculum) in the supernatant and the cells overlain for a further 48 hours with two milliliters of complete media and the virus was harvested (second inoculum). The second supernatant was used as an inoculum in experiments to determine the optimum time of expression of the proteins. For all infections, media was aspirated from the cells and the cells overlain with 250 μl of inoculum for one hour (m.o.=5). At the end of one hour the inoculum was discarded and the cells overlain with two milliliters of complete TC-100 media supplemented with 10% fetal calf serum. Protein expression was analysed over a period of 60 hours. At the end of each analysis period the cells were lysed using protein disruption buffer (62.5 mM Tris-HCl, 2% SDS). Fifteen microliters of protein sample was then loaded on a 12.5% polyacrilamide gel and western blot analysis was done with either anti-ricin toxin B chain antibodies or anti-CryIA(c) antisera.

Result of western blot analysis for protein expression.

Baculovirus protein expression was analysed over a period of 60 h. Cell samples were collected at 2, 20, 24, 34, 48, and 60 hours p.i. and protein concentrations determined using the dye binding method (47). Protein samples (20 μg) were fractionated by 12.5% SDS-PAGE and transferred to nitrocellulose membranes (Hybond C; Amersham) using the Trans-Blot semidry transfer cell (Bio-Rad) according to the manufacturer's instructions. Filters were probed with antisera against Cry1Ab and Cry1Ac (Ms. S. Bano-Maqbool, Centre for Excellence in Plant Molecular Biology, Pakistan) or RTB (Dr. L. Roberts, University of Warwick, UK). We used alkaline phosphatase (AP)-conjugated anti-rabbit IgG (Fc) as the secondary antibody (Promega) and detection was carried out according to the supplier's recommendations.

For RTB1, RTB2 and RTB3 (control constructs containing only the ricin toxins fragments), protein expression started at about 20 hours post infection and increased gradually up to 60 hours, being optimised around 34 hours. Protein bands of lower molecular weight than expected, presumably representing degradation products, were detected at 48 hours (RTB1), 34 hours (RTB2) and 24 hours RTB3. Thus the third ricin toxin B chain gene deletion, RTB3, in particular, appears to be unstable and degrades after synthesis As for the cryIA(a) and cryIA(c) genes together with the fusion proteins, degradation products were detected as early as 20 hours, suggesting that the proteins were sensitive to degradation in insect cells.

Example 4

In vitro Toxicity Assays

Determination of optimal fluorophore concentration.

Optimal dye concentrations vary with cell types. The following experiment was done to find out the lowest dye concentration that gives sufficient signal. Healthy growing cells were harvested into microfuge tubes and washed once with 1000 µl of Dulbecco's phosphate buffered saline. Half of these cells were killed using 30% methanol for 30 minutes. Using samples of dead cells and live cells separately, an aliquote of the cells were each incubated with a different concentration of the Ethidium homodimer 1 from 0.1–12.8 µM for 30 minutes. Separate samples of live and dead cells were also incubated with various levels of Calcein AM (0.1–12.8 µM). The stained cells were visualised under a conventional fluorescein microscope. A concentration of 6.8 µM of Ethidium homodimer 1 sufficiently labelled the nuclei of dead cells bright red. A concentration of 0.4 µM of Calcein AM sufficiently labelled live cells green. The two fluorophores were then mixed together to achieve a solution consisting of 6.8 µM Ethidium homodimer 1 and 0.4 µM Calcien AM in D-PBS and used to stain samples of dead and live cells. From these results it was concluded that the two fluorophores at the selected concentrations can be reliably used to assess the viability of infected cells.

Live/Dead viability/Cytotoxicity assays over 96 hours.

A million cells were seeded in 35 mm culture dishes overnight for each infection (seven replications each). The media was aspirated from the cells and the cells were overlain with 250 µl inoculum. Fourteen different infections carried out included:
(a) insect cells mock infected with media
(b) insect cells infected with non-recombinant baculovirus
(c) insect cells infected with recombinant baculovirus containing the gus gene
(d) insect cells infected separately with recombinant baculovirus containing the coding sequence of CryIA(b), CryIA(c), RTB1, RTB2 and RTB3.
(e) insect cells infected separately with the six different fusion genes.

Infected cells were lysed and DNA extracted from them at 34 hours post infection. The composition of the lysis buffer and the method of extraction were according to King and Possee (38). This DNA was used to verify success of infection of the Sf21 insect cells in PCR reactions utilising the M13/PUC primers. Infected cells from one culture dish for each infection were analysed for viability at 2, 24, 34, 48, 72 and 96 hours post infection. The cells were pelleted at 5 000 ×g and washed once with sterile tissue culture-grade Dulbecco's phosphate-buffered saline (D-PBS). The cells were gently resuspended in 50 µl of the live/dead assay reagent (6.8 µM Ethidium homodimer 1 and 0.4 µM Calcein AM, made up in D-PBS) and incubated at room temperature for 30 minutes. After the 30 minutes, 40 µl of the assay reagent was removed from the cells and discarded. The cells if undisturbed, by now would have settled at the bottom of the microfuge tubes. The remaining 10 µl, concentrated with cells was put on a microscope slide and photographed under the fluorescein microscope (485±11 nm) at a magnification of ×400.

Ethidium homodimer-1 binds tightly to DNA and fluoresces deep red, but it is a hydrophilic molecule and cannot cross living cell membranes. Calcein AM is a neutral molecule that diffuses freely into cells. It is cleaved by intracellular esterase activity and fluoresces bright green. Ethidium homodimer-1 thus labels the nuclei of dead cells, whereas calcein AM labels the cytosol of living cells.

Two photograph sets, one for the Ethidium homodimer 1 fluorescence and the other for the Calcein AM fluorescence were taken by switching alternately the two filter sets so that each cell sample had a photograph showing the proportion of cells that are still alive (green fluorescence) and another showing the proportion of cells that are dead (red fluorescence).

Results of Toxicity Assays

When viewed under an inverted light microscope (×400) cells infected with the fusion proteins exhibited a number of symptoms of toxicity as early as 24 hours post infection. The symptoms included, floating in the media, large spherical shapes and lysed cells. Some of the symptoms, particularly cell lysis, appeared later than 60 hours post infection in the control experiments. The controlled experiments included cells mock infected with media, cells infected with baculovirus only and cells infected with recombinant baculovirus containing the gus gene and the ricin toxin B cain gene fragments only. In the live/dead viability assays on the Sf21 insect cells infected with recombinant baculoviruses expressing different proteins, cells which gave green fluorescence had esterase activity and so were assessed as alive, while cells giving red fluorescence had compromised membranes and were assessed as dead.

The results of the assays can be summarised as follows:
(a) the assay was tested with healthy Sf21 insect cells. Uninfected cells were left for 72 hours undisturbed and without change of media. Very few cells were observed dead when assessed as described above. When healthy cells were treated with 70% methanol for 30 mins all the cells were observed dead.
(b) Sf21 insect cells infected with baculovirus only were assessed after 2 hrs, 24 hrs, 34 hrs and 72 hrs post infection. Many cells were still alive after 72 hours.
(c) Sf21 insect cells expressing GUS activity were assessed after 2, 24, 34, 72 hrs post infection. Again many cells are still alive after 72 hrs.
(d) Sf21 insect cells expressing CryIA(b) were assessed after 2, 24, 34, 72 hrs post infection. The cells were seriously affected by this protein between 34–72 hrs.
(e) Sf21 insect cells expressing CryIA(c) were assessed after 2, 24, 34, 72 hrs post infection. Again the cells are also seriously affected by this protein between 23–72 hrs.
(f) Sf21 insect cells expressing RTB1 protein were assessed after 2, 24, 34, 72 hrs post infection. Many cells were still alive after 72 hrs.
(g) Sf21 cells expressing CryIA(b)-RTB1 fusion protein were assessed after 2, 24, 34, 72 hrs post infection. The cells were seriously affected between 24–34 hrs post infection.
(h) Sf21 cells expressing CryIA(c)-RTB1 fusion protein were assessed after 2, 24, 34, 72 hrs post infection. The cells were seriously affected between 24–34 hrs.
(i) Sf21 cells expressing RTB2 protein were assessed after 2, 24, 34, 72 hrs post infection. Many of the cells were still alive after 72 hrs.

(j) Sf21 cells expressing CryIA(b)-RTB2 protein were assessed after 2, 24, 34, 72 hrs post infection. By 24 hrs many cells are dead i.e. much earlier than in the above assays.

(k) Sf21 cells expressing CryIA(c)-RTB2 protein were assessed after 2, 24, 34, 72 hrs post infection. A significant number of the cells were dead by 24 hrs; again earlier than with the toxin alone.

(l) Sf21 cells expressing RTB3 protein after were assessed 2, 24, 34, 72 hrs post infection. Many cells were still alive after 72 hrs.

(m) Sf21 cells expressing CryIA(b)-RTB3 fusion protein were assessed after 2, 24, 34, 72 hrs post infection. Many cells were dead by 24 hrs, although some cells survived until 72 hrs.

(n) Sf21 cells expressing CryIA(c)-RTB3 fusion protein were assessed after 2, 24, 34, 72 hrs post infection. Many of the cells survived until 72 hrs.

Insect epithelial cell cultures are not natural targets for Bt d-endotoxins and their toxin sensitivities are several orders of magnitude lower than those observed in the insects from which they originate[23]. However, cell cultures are routinely used to estimate the activity of Bt toxins against various insect species[24].

Although the most severe symptoms were observed in insect cells infected with fusion proteins containing RTB1 and RTB2, the fusion of any of the three different RTB fragments to either Cry1Ab or Cry1Ac resulted in greatly increased toxin sensitivity in Sf21 cells when assayed for viability using the Ethidium homodimer 1 and Calcein AM. Toxicity symptoms were observed at about 34 hours post infection. It is clear that the fusion proteins have severe cytotoxic effects on the insect cells producing them, and it is also clear that the addition of the glycosylation-binding (ricin toxin B chain) gene to the toxin enhances this toxicity, as measured by premature cell death and extensive cell lysis.

The choice of the toxins Cry1Ab and Cry1Ac and the use of Sf21 cells was based on earlier observations that Cry1Ab is moderately toxic to Sf9 and IPLB-Sf21 insect cells while Cry1Ac has no effect on these cells (42, 43). Clearly, the acquisition of toxicity by Cry1Ac when combined with the ricin toxin B-chain suggests a role for galactose-binding in the mediation of toxicity.

Example 5

Use of Insecticidal Fusions in Plants

Fusion proteins may be transformed into plants, for instance maize or rice, as follows. The sequence encoding the fusion polypeptide is inserted into an expression cassette under the control of a ubiquitin promoter. Plants are transformed using particle bombardment (see e.g. Christenson et al (1992) Plant Mol Biol 18:675–689; Christou et al (1991) Bio/Technol 16: 957–962). The plants may then be used in insect feeding bioassays to assess the toxicity of the fusions at the whole organism level and to measure resistance under conditions of varied selection pressure. Plants may also be assessed for transgene integration and expression patterns, and the expression product may be purified using standard protocols. An example with rice is given below.

Overview of Generation of Bt-transgenic Rice Plants

Mature seed-derived embryogenic rice callus was transformed with the 11 constructs (six fusions and five controls) shown in FIG. 1B. Each construct was introduced into rice tissue by particle bombardment, along with a co-transformation vector allowing selection for hygromycin resistance. Further analysis was carried out on plants expressing equivalent amounts of the 11 recombinant proteins. The fusion proteins were expressed more efficiently in transgenic rice plants than in baculovirus-infected insect cells as were the unmodified Bt proteins.

Transgene Constructs

The control and fusion protein cassettes described above were isolated from the intermediate pFASTBAC Hb vectors using EheI and HindIII, and directionally subcloned in pAL76 (an in-house ubiquitin promoter-based transformation vector) digested with SmaI and HindIII (FIG. 1C).

Particle Bombardment and Recovery of Transgenic Plants

Mature rice seeds (*Oryza staiva* L. cv Eyi105) were de-hulled and washed in 70% ethanol for 2 min. After rinsing twice in distilled water, the seeds were sterilised in 1.6% sodium hypochlorite for 30 minutes with gentle agitation, then rinsed three times in sterile distilled water. The seeds were germinated in darkness on rice callus induction medium (RCIM; MS basal medium supplemented with 2.5 mg $l^{-1}$ 2, 4-D and solidified with 2.5 g $l^{-1}$ phytagel). After 7 days, scutellum-derived callus was dissected from the germinating seeds and cultured in darkness on osmoticum medium (RCIM supplemented with 36 g $l^{-1}$ sorbitol and 36 g $l^{-1}$ mannitol (48) for 4 h. The callus was then bombarded with 0.95 mm diameter gold particles coated with DNA. Bombardment was carried out twice with a 4-h interval, and the callus was co-bombarded with one of the 11 plasmids containing fusion or control constructs and a cotransformation plasmid containing a marker conferring hygromycin resistance (49), at a molar ratio of 1:3. Particle coating and bombardment procedures were described earlier (50, 51). After the second bombardment, callus was incubated in darkness on the osmoticum medium for a further 16 h and then transferred to RCIM for three days. The callus was then transferred to selection medium (RCIM supplemented with 30 mg $l^{-1}$ hygromycin B) for 4 weeks. Subcultures were carried out at 2-week intervals. Hygromycin resistant callus was transferred to HRSM1 medium in daylight (MS basal medium supplemented with 30 g $l^{-1}$ maltose, 2 mg $l^{-1}$ BAP, 0.5 mg $l^{-1}$ NAA, 30 mg $l^{-1}$ hygromycin B and 5 g $l^{-1}$ gelrite gellan gum) to initiate shoot regeneration. After one week, the regenerating callus was transferred to HRSM2 medium (as HRSM1 but with only 2.5 g $l^{-1}$ gelrite gellan gum) and cultured under the same conditions. Fully regenerated shoot systems were transferred to rooting medium HRRM (½ MS basal medium supplemented with 10 g $l^{-1}$-sucrose). Mature plants were transferred to the glasshouse.

RT-PCR Analysis

Total RNA was extracted from 100 mg leaf tissue of transformed and wild type rice plants using the Rneasy Plant Mini kit (Qiagen) according to the supplier's recommendations. RT-PCRs were carried out using the Access-PCR kit (Promega) according to the manufacturer's instructions. We used 100 ng total RNA and 50 pmol of each primer. Primers CRF1 and CRR1 amplify both cry1Ab and cry1Ac, while primers RTF1 and RTR1 amplify the RTB gene fragment. The primer sequences were as follows: CRF1 (5'-CGCAT-TGAAAC CGGTTACACTC CCA-3' (Seq ID No 16)), CRR1 (5'-CTTGGGCAGAACCACGGAAGCTACC-3' (Seq ID No 17)), RTF1 (5'-GATGTTTGTATGGATCCT-CAGCCCA-3' (Seq ID No 18)) and RTR1 (5'-GCCGAA-CAATGGTTGTAACAAAAGG-3' (Seq ID No 19)).

Northern Blots

Total RNA was extracted as described above, and 15 mg aliquots were fractionated by electrophoresis on 1% agarose-formaldehyde gels and transferred to nitrocellulose filters according to standard procedures (52). We labeled 1.8 kbp BamHI/EcoRI fragments corresponding to the cry1Ab and cry1Ac coding regions, for use as probes.

Western Blot Analysis

Western blot analysis of transgenic plants was carried out on small leaf sections ground to a fine powder under liquid nitrogen. Samples were dispersed in protein extraction buffer (100 mM Tris.Cl pH 8.1, 100 mM 2-mercaptoethanol) and centrifuged at 12,000×g for 10 min at 4° C. SDS-PAGE was carried out using 30 mg samples, and blotting and detection procedures were carried out as described above.

Analysis of banding patterns on western blots suggested that fusion proteins containing the longest RTB fragment (RTB1) were the most stable. The control RTB fragments were also efficiently expressed in transgenic rice plants. The presence of transgene mRNAs in the plants was confirmed by northern blot analysis and RT-PCR (data not shown).

Thus it is clear that the fusion proteins were efficiently expressed in transgenic rice plants.

Example 6

Insect Bioassays

Overview of Insect Bioassays

Insect bioassays were performed using stem sections of wild type control plants and transgenic lines individually transformed with nine of the 11 constructs (six fusions and five controls) shown in FIG. 1B. Plants transformed with pR2 or pR3 (control constructs containing the shorter RTB fragments) were not tested. The effect of these control and fusion proteins was determined on an economically important rice pest, the striped stem borer.

Insect Bioassays

A culture of striped stem borer eggs (Chilo suppressalis) was obtained from Dr M. Cohen, International Rice Research Institute, The Philippines. Eggs were maintained under a 27/25° C. day/night temperature regime with a 16-h photoperiod. The insects were held under a MAFF licence EPHL 51/2595(3/1998). Rice plants were grown and maintained under identical conditions.

Bioassays were carried out on stem sections from primary transformants and wild type controls. A single stem section, 7 cm long with at least one node, was taken from each plant. Sections were placed on moist filter paper in dishes and infested with neonate stem borer larvae (<2 h old) by placing three at each end of the cut sections to facilitate entry into the stem. Four replicates were set up for each line, except the wild type control, where eight replicates were used. The dishes were then sealed with Parafilm and left for 4 days in a controlled growth chamber under the conditions specified above. After the trial period, stem sections were dissected under a binocular microscope and insect survival, development and weight were recorded. Statistical analysis of insect data was performed with Statview software v. 5.0 (Abacus Concepts, CA). Analysis of variance (ANOVA) was used to test for significant differences between treatments. A rejection limit of p>0.05 was used.

Results

The results are shown in FIG. 2. Insect survival on wild type control stem sections was >95%.

On plants expressing the unmodified Cry1Ab and Cry1Ac toxins, insect survival decreased to between 55 and 80% (mean values of 79% (Cry1Ab) and 71% (Cry1Ac)). The data suggested that Cry1Ac was slightly more toxic towards the stem borer than Cry1Ab, although the difference was not statistically significant. There was no significant effect on insect survival in line pR1, expressing the RTB1 control fragment, although surviving larvae showed impaired growth (see below).

With the exception of plants transformed with construct pBR3, the mean insect survival on all plants expressing fusion proteins was significantly lower than that of wild type control plants and plants expressing control proteins.

Plants transformed with constructs pCR1, pCR2 and pCR3 were highly resistant to the stem borer, with insect mortalities of 87%, 74% and 61% respectively.

The results for plants transformed with constructs pBR1, pBR2 and pBR3 were more variable, with survival in the range of 30–50%, and pBR2 the most effective.

Surviving larvae showed impaired growth and developmental arrest in all transgenic lines. Mean larval weight fell by 30% in plants expressing the control Bt proteins and the control RTB fragment. Developmental arrest was more severe in plants expressing Cry1Ac than in plants expressing Cry1Ab.

Of the Cry1Ab fusion proteins, only pBR1 had a significantly greater effect than the control Bt protein Cry1Ab, causing a 60% reduction in mean larval weight. Severe reductions in larval growth and development were also observed in plants expressing pCR1, pCR2 and pCR3. The results with pCR2 and pCR3 were similar to those for pBR1, but pCR1 was again the most effective construct, causing a mean larval weight decrease of >80% and preventing development beyond the first instar.

Thus transgenic rice plants expressing the fusion proteins were fully protected against feeding by the stripped stem borer, causing insect mortalities of 55–80% and poor growth and arrested development in surviving larvae. The most toxic fusion protein was pCR1. After four days there was 87% insect mortality and developmental arrest at the first instar stage in surviving larvae. After four days, larvae feeding on wild type rice plants had reached the third instar and had caused severe damage to the stems. Conversely, larvae feeding on transgenic plants expressing the fusion proteins did not cause significant damage. The addition of a galactose binding domain to the Bt toxins therefore significantly enhanced their activity against the stripped stem borer.

Conclusions

These Examples clearly show that a heterologous binding domain which is non-toxic per se but which is capable of binding non-specifically to a cell membrane without disrupting that membrane (e.g. the ricin toxin B chain) when combined with a toxin (e.g. the d-endotoxins Cry1Ab and Cry1Ac) can increase the range of molecular interactions available to the toxins thereby potentially broadening the spectrum of their activity. In particular the Examples show an increased toxicity compared to the unmodified toxin both in vitro (towards Sf21 cells) and in vivo (towards the striped stem borer). Additionally, the addition of a novel binding domain is likely to delay or prevent the evolution of resistance in insect populations, as insects are less likely to undergo mutations that abolish two or more distinct cellular uptake activities.

Example 7

Binding of Lectins, Bt Toxin and Bt-lectin Fusions to Insect Gut Polypeptides Methodology Briefly, guts were dissected from two insect pests of rice, the striped stem borer used for the insect bioassays described above, and a homopteran species, rice brown planthopper (*Nilaparvata lugens*). Extracted gut polypeptides were separated by SDS-polyacrylamide gel electrophoresis, blotted and probed with lectins, Bt toxin, or Bt-lectin fusion protein; bound probe was then detected by suitable specific antibody.

In more detail, a construct encoding a His-tagged fusion of domain 1 of the Bt toxin Cry1Ac and snowdrop lectin (GNA) (designated JD1) was first expressed in *E. coli*. The fusion protein was purified by chromatography on Ni-NTA agarose beads (Qiagen) after solubilization, dialysed to remove denaturants, and concentrated by ultrafiltration to give a preparation of soluble, functional protein. The final concentration and purity were estimated by SDS-PAGE. Brown planthopper (*Nilapavata lugens*) midguts were dissected from insects freshly collected from rice plants, and homogenized in SDS sample buffer by sonication. Striped stem borer midguts (provided by Dr. Mike Cohen, IRRI' were collected from late-instar larvae and were treated similarly. Solubilised gut protein was then separated by SDS-PAGE (12.5% acrylamide) and transferred onto nitrocellulose membranes. The amount of protein loaded was equivalent to 1.5 guts per lane for brown planthopper; for striped stem borer, approx. 5 µg of protein was loaded per lane. After incubation in blocking reagent (Sigma) for 60 minutes, membranes containing the gut proteins were probed by incubation with JD1, Cry1Ac (a gift from Dr. David Ellar; the protoxin was activated by trypsin treatment as described (53), GNA (Drs. W. Peumans and E. van Damme, Catholic University of Leuven, Belgium) or *Ricinus communis* agglutinin (Sigma) respectively. Incubation was carried out for 60 minutes at 25° C., at a concentration of 1 µg ml$^{-1}$. Membranes were washed three times, 5 min per wash, with 20 ml Tris-buffered Triton-saline (TBS-T; 50 mM Tris-HCl buffer, pH 7.2, containing 0.15 M NaCl and 0.1% Triton X-100). Ligand binding was then detected by incubation with the appropriate primary antibody (anti-Cry1Ac, a kind gift from Dr. David Ellar; anti-GNA, produced by the authors; anti-*Ricinus communis* agglutinin, Vector Labs) in TBS-T at 1:10,000 dilution of for 60 minutes at 25° C. The membrane was washed again as above and incubated with the secondary antibody (HRP-conjugated; Bio-Rad) at a dilution of 1:5000. The membrane was washed again as above and further rinsed in distilled water twice before ECL reagents (Amersham Pharmacia Biotech, UK) were added, and the blot was exposed to X-ray film following the manufacturer's instructions.

Results

The combination of *Ricinus communis* lectin as a probe and anti-*Ricinus communis* lectin antibodies as a detection reagent showed strong binding to a large number of polypeptides in extracts from gut tissues of both insects. In contrast, the Cry1Ac protein probe only bound strongly to one polypeptide in the same extracts (approx. 45 kDa in striped stem borer and 90 kDa in brown planthopper). To further characterise differences in binding between Bt toxin and a Bt-lectin fusion, a fusion protein between the specific mannose-binding lectin from snowdrop (*Galanthus nivalis* agglutinin; GNA) and Cry1Ac was produced by expression of a suitable gene construct in *E. coli*. Binding of the fusion protein to insect gut polypeptides was then compared to that of GNA and Cry1Ac proteins separately. In agreement with previous results, GNA bound strongly to polypeptides of about 75 kDa (2 bands) and 50 kDa extracted from rice brown planthopper gut, and bound strongly to a polypeptide of approx. 80 kDa from striped stem borer gut. GNA also bound to a 45-kDa polypeptide in stem borer gut extracts, a similar molecular weight to the major band detected by Cry1Ac. The GNA-Cry1Ac fusion bound only very weakly to the 85-kDa polypeptide recognised by GNA in striped stem borer gut, but bound to the 45-kDa polypeptide recognised by both GNA and Cry1Ac toxin. On the other hand, the fusion showed binding to all the major polypeptides recognised by GNA and by Cry1Ac toxins in brown planthopper gut extracts (approximately 90 kDa, 75 kDa and 45 kDa). These results show that the lectin-Bt fusions have different binding specificities to polypeptides extracted from insect gut tissues, compared to the Bt toxin from which they are derived.

Discussion

In the experiments above, purified lectins, Bt toxins and Bt-lectin fusion proteins were allowed to react with polypeptides extracted from insect guts. The results showed that the galactose-binding domain in ricin binds strongly to many more polypeptides in insect gut extracts than Cry1Ac toxin. The bifunctional nature of the binding of lectin-Bt fusion proteins (i.e. with binding properties which are derived from both the contributing protein domains) was shown directly by binding assays with a purified GNA-Cry1Ac fusion protein on polypeptides from insect guts.

REFERENCES

1. Monette et al. (1997). Applied and Environmental Microbiology 63 (2), 440–447.
2. Luckow, (1991). Cloning and expression of heterologous genes in insect cells with baculovirus vectors, p. 97–151. Prokop et al., (Ed), Recombinant DNA technology and applications. McGraw-Hill, New York, N.Y.
3. Ferrini et al., (1995) European Journal of Biochemistry 233, 772–777.
4. Ge et al., (1991). The Journal of Biological Chemistry 266 (27), 17954–17958.
5. Schnepf and Whitley, (1985). The Journal of Biological Chemistry 260, (10), 6273–6280.
6. Dean et al., (1996) Gene 179, 111–117.
7. Weyer et al., (1990). Journal of General Virology 71, 1525–1534.
8. Martens et al., (1990). Applied and Environmental Microbiology 56 (9), 2764–2770.
9. Merryweather et al., (1990). Journal of General Virology 71, 1535–1544.
10. Miller, (1988). Annual Review of Microbiology 42, 177–199.
11. Pang et al., (1992). Journal of General Virology 73, 89–101.
12. Hofmann et al., (1988). Proc. Natl. Acad. Sci. USA 85, 7844–7844.
13. Vadlamudi et al., (1995). The Journal of Biological Chemistry 270 (10) 5490–5494.
14. Lee et al., (1996). Applied and Environmental Microbiology 62 (8) 2845–2849.
15. Masson et al., (1995). The Journal of Biological Chemistry 270 (35), 20309–20315.

16. Tabashnik et al., (1997). Proc. Natl. Acad. Sci. 94, 1640–1644.
17. Tabashnik, (1994). Annual Review of Entomology 39, 47–79.
18. Tabashnik et al. Applied and Environmental Microbiology 62 (8) 2839–2844.
19. Perlak et al., (1990). Bio/Technology 8, 939–943.
20. Vaek et al., (1989). Cell Cult. Somatic Genet. Plants 6, 425–439.
21. Vaek et al., (1987). Nature 327, 33–37.
22. Cornelissen, (1989). Nucleic Acids Research 17, 7203–7209.
23. Perlak et al., (1991). Proc. Natl. Acad. Sci 88, 3324–3328.
24. Arsine et al., (1995). Plant Molecular Biology 28, 513–524.
25. Murray et al., (1989). Nucleic Acids Research 17, 477–498.
26. Wolin and Walter, (1988). Embo Journal 7, 3559–3569.
27. Koziel et al., (1993). Bio/Technology 11, 194–199.
28. Dellaporta and Calderon-Urrea, (1994). Science 266, 1501–1505.
29. Irish, (1996). BioEssays 18 (5), 363–369.
30. Heslop-Harrison, (1961). Proc. Linn. Soc., London. 172, 108–123.
31. Hansen et al., (1976). Crop Science. 16, 371–374.
32. Morino et al., (1995). Biol. Pharm. Bull. 18 (12) 1770–1772.
33. Endo and Tsurugi, (1987). J. Biol. Chem. 262, 8128.
34. Wales et al., (1992). Archives of Biochemistry and Biophysics 294 (1), 291–296.
35. Wales et al., (1991). The Journal of Biological Chemistry 266 (29), 19172–19179.
36. Sardana et al., (1996). Plant Cell Reports 15, 677–681.
37. GIBCO (1996). BAC-TO-BAC™ baculovirus expression systems: Instruction Manual, 1–33.
38. King and Possee, (1990). The baculovirus expression system: A laboratory guide. Chapman and Hall, 143–144.
39. Molecular probes product information sheet, live/dead viability/cytotoxicity kit (L-3224), ppl._
40. Glaze and Rye (1992) Nature 359: 859–861.
41. Bell et al (1988) *J. Orthopaedic Res.* 6: 467–474.
42. Johnson (1994) *J. Invertebr. Pathol.* 63: 123–129.
43. [see 1]
44. Newton et al (1992) *J. Biol. Chem.* 267: 11917–11922.
45. Gonatas et al (1975) *Exp. Cell Res.* 94: 426–431.
46. [see 36]
47. Bradford (1976) *Annal. Biochem.* 72: 248–254.
48. Vain et al (1993) *Plant Cell Rep.* 12: 84–88.
49. Cooley et al (1995) *Theoret. Appl. Genet.* 90, 97–104.
50. Klein et al (1988) Proc. Natl. Acad. Sci. USA. 85: 4305–4309
51. Sudhakar et al (1998) *Transgenic Res.* 7: 289–294
52. Sambrook et al (1989). Molecular Cloning: A Laboratory Manual. Second edition, Cold Spring Harbour Lab. Press.
53. Knight et al (1994) *Mol. Microbiol.* 11: 429–436.

The invention claimed is:

1. A nucleic acid molecule encoding a pesticidal fusion polypeptide comprising
   i) a toxin domain and
   ii) a binding domain, wherein said nucleic acid comprises the CryIA-RTB combination shown in any one of Seq ID NO: 6 (CryIA(b)-RTB1); Seq ID NO:7 (CryIA(b)-RTB2); Seq ID NO: 8 (CryIA(b)-RTB3); Seq ID NO:9 (CryIA(c)-RTB1); Seq ID NO:10 (CryIA(c)-RTB2); and Seq ID NO:11 (CryIA(c)-RTB3).

2. A method of producing the nucleic acid of claim 1, wherein the method comprises the step of joining a nucleic acid molecule selected from the group consisting of SEQ ID NO:1 and SEQ ID NO:2 with a nucleic acid molecule selected from the group consisting of SEQ ID NO:3, SEQ ID NO:4 and SEQ ID NO:5.

3. A recombinant vector comprising the nucleic acid as claimed in claim 1.

4. The vector as claimed in claim 3 wherein said nucleic acid is operably linked to a promoter.

5. The vector as claimed in claim 4 wherein the promoter is an inducible promoter which is switched on in response to an elicitor or other plant signal which is triggered in response to predation.

6. The vector as claimed in claim 3, which is a baculovirus vector or a vector suitable for use in a plant.

7. A method for transforming a host cell, wherein the method comprises the step of introducing a vector of claim 3 into the cell and causing or allowing recombination between the vector and the cell genome to introduce the nucleic acid into the genome.

8. A host cell containing the nucleic acid of claim 1.

9. A host cell transformed with the nucleic acid of claim 1.

10. The host cell as claimed in claim 8 which is a plant cell.

11. The host cell as claimed in claim 10, wherein said plant cell is from a monocot plant.

12. The host cell as claimed in claim 11, wherein said monocot plant is maize or rice.

13. A process for producing a transgenic plant, wherein the process comprises the steps of:
   (a) transforming a plant cell by introducing a recombinant vector comprising the nucleic acid as claimed in claim 1 into said plant cell and causing or allowing recombination between the vector and the cell genome to introduce the nucleic acid into the genome, thereby producing a transformed plant cell; and
   (b) regenerating a plant from said transformed host cell.

14. A plant obtainable by the process of claim 13, which comprises the nucleic acid molecule.

15. A plant which is a clone, selfed or hybrid progeny, or other descendant of the plant of claim 14, wherein the clone, selfed or hybrid progeny, or other decendant comprises the nucleic acid molecule.

16. The plant as claimed in claim 14 which is a monocot.

17. The plant as claimed in claim 16, wherein the monocot is maize or rice.

18. A part or propagule of the plant of claim 14.

19. A method of influencing or affecting the toxicity of a plant to a pest, wherein the method comprises transforming a plant with the nucleic acid of claim 1.

20. A host cell containing the vector of claim 3.

21. A host cell transformed with the vector of claim 3.

22. The host cell as claimed in claim 9 which is a plant cell.

23. The host cell as claimed in claim 22, wherein said plant cell is from a monocot plant.

24. The host cell as claimed in claim 23, wherein said monocot plant is maize or rice.

* * * * *

SEQUENCE LISTING

```
<160> NUMBER OF SEQ ID NOS: 19

<210> SEQ ID NO 1
<211> LENGTH: 2062
<212> TYPE: DNA
<213> ORGANISM: Artificial Sequence
<220> FEATURE:
<223> OTHER INFORMATION: Description of Artificial Sequence: Nucleotide
      sequence of CryIA(b) in pFASTBAC1

<400> SEQUENCE: 1
aaataagtat tttactgttt tcgtaacagt tttgtaataa aaaaacctat aaatattccg      60
gattattcat accgtcccac catcgggcgc ggatccatgg acaacaaccc aaacatcaac     120
gaatgcattc catacaactg cttgagtaac ccagaagttg aagtacttgg tggagaacgc     180
attgaaaccg gttacactcc catcgacatc tccttgtcct tgacacagtt tctgctcagc     240
gagttcgtgc caggtgctgg gttcgttctc ggactagtta acatcatctg gggtatcttt     300
ggtccatctc aatgggatgc attcctggtg caaattgagc agttgatcaa ccagaggatc     360
gaagagttcg ccaggaacca ggccatctct aggttggaag gattgagcaa tctctaccaa     420
atctatgcag agagcttcag agagtgggaa gccgatccta ctaacccagc tctccgcgag     480
gaaatgcgta ttcaattcaa cgacatgaac agcgccttga ccacagctat cccattgttc     540
gcagtccaga actaccaagt tcctctcttg tccgtgtacg ttcaagcagc taatcttcac     600
ctcagcgtgc ttcgagacgt tagcgtgttt gggcaaaggt ggggattcga tgctgcaacc     660
atcaatagcc gttacaacga ccttactagg ctgattggaa actacaccga ccacgctgtt     720
cgttggtaca cactggctt ggagcgtgtc tggggtcctg attctagaga ttggattaga     780
tacaaccagt tcaggagaga attgaccctc acagttttgg acattgtgtc tctcttcccg     840
```

-continued

| | |
|---|---|
| aactatgact ccagaaccta ccctatccgt acagtgtccc aacttaccag agaaatctat | 900 |
| actaacccag ttcttgagaa cttcgacggt agcttccgtg gttctgccca aggtatcgaa | 960 |
| ggctccatca ggagcccaca cttgatggac atcttgaaca gcataactat ctacaccgat | 1020 |
| gctcacagag gagagtatta ctggtctgga caccagatca tggcctctcc agttggattc | 1080 |
| agcgggcccg agtttacctt tcctctctat ggaactatgg gaaacgccgc tccacaacaa | 1140 |
| cgtatcgttg ctcaactagg tcaggtgtc tacagaacct tgtcttccac cttgtacaga | 1200 |
| agacccttca atatcggtat caacaaccag caactttccg ttcttgacgg aacagagttc | 1260 |
| gcctatggaa cctcttctaa cttgccatcc gctgtttaca gaaagagcgg aaccgttgat | 1320 |
| tccttggacg aaatcccacc acagaacaac aatgtgccac ccaggcaagg attctcccac | 1380 |
| aggttgagcc acgtgtccat gttccgttcc ggattcagca cagttccgt gagcatcatc | 1440 |
| agagctccta tgttctcatg gattcatcgt agtgctgagt tcaacaatat cattccttcc | 1500 |
| tctcaaatca cccaaatccc attgaccaag tctactaacc ttggatctgg aacttctgtc | 1560 |
| gtgaaaggac caggcttcac aggaggtgat attcttagaa gaacttctcc tggccagatt | 1620 |
| agcaccctca gagttaacat cactgcacca ctttctcaaa gatatcgtgt caggattcgt | 1680 |
| tacgcatcta ccactaactt gcaattccac acctccatcg acggaaggcc tatcaatcag | 1740 |
| ggtaacttct ccgcaaccat gtcaagcggc agcaacttgc aatccggcag cttcagaacc | 1800 |
| gtcggtttca ctactccttt caacttctct aacggatcaa gcgttttcac ccttagcgct | 1860 |
| catgtgttca attctggcaa tgaagtgtac attgaccgta ttgagtttgt gcctgccgaa | 1920 |
| gttaccttcg aggctgagta ctgagaattc aaaggcctac gtcgacgagc tcactagtcg | 1980 |
| cggccgcttt cgaatctaga gcctgcagtc tcgaggcatg cggtaccaag cttgtcgaga | 2040 |
| agtactagag gatcataatc ag | 2062 |

<210> SEQ ID NO 2
<211> LENGTH: 2062
<212> TYPE: DNA
<213> ORGANISM: Artificial Sequence
<220> FEATURE:
<223> OTHER INFORMATION: Description of Artificial Sequence: Nucleotide
    sequence of CryIA(c) in pFASTBAC1

<400> SEQUENCE: 2

| | |
|---|---|
| aaataagtat tttactgttt tcgtaacagt tttgtaataa aaaaacctat aaatattccg | 60 |
| gattattcat accgtcccac catcgggcgc ggatccatgg acaacaaccc aaacatcaac | 120 |
| gaatgcattc catacaactg cttgagtaac ccagaagttg aagtacttgg tggagaacgc | 180 |
| attgaaaccg gttacactcc catcgacatc tccttgtcct tgacacagtt tctgctcagc | 240 |
| gagttcgtgc caggtgctgg gttcgttctc ggactagttg acatcatctg gggtatcttt | 300 |
| ggtccatctc aatgggatgc attcctggtg caaattgagc agttgatcaa ccagaggatc | 360 |
| gaagagttcg ccaggaacca ggccatctct aggttggaag gattgagcaa tctctaccaa | 420 |
| atctatgcag agagcttcag agagtgggaa gccgatccta ctaacccagc tctccgcgag | 480 |
| gaaatgcgta ttcaattcaa cgacatgaac agcgccttga ccacagctat cccattgttc | 540 |
| gcagtccaga actaccaagt tcctctcttg tccgtgtacg ttcaagcagc taatcttcac | 600 |
| ctcagcgtgc ttcgagacgt tagcgtgttt gggcaaaggt ggggattcga tgctgcaacc | 660 |
| atcaatagcc gttacaacga ccttactagg ctgattggaa actacaccga ccacgctgtt | 720 |
| cgttggtaca cactggcttg ggagcgtgtc tggggtcctg attctagaga ttggattaga | 780 |

-continued

```
tacaaccagt tcaggagaga attgaccctc acagttttgg acattgtgtc tctcttcccg      840
aactatgact ccagaaccta ccctatccgt acagtgtccc aacttaccag agaaatctat      900
actaacccag ttcttgagaa cttcgacggt agcttccgtg ttctgccca aggtatcgaa       960 ggctccatca ggagcccaca cttgatggac atcttgaaca gcataactat ctacaccgat     1020
gctcacagag gagagtatta ctggtctgga caccagatca tggcctctcc agttggattc     1080
agcgggcccg agtttacctt tcctctctat ggaactatgg gaaacgccgc tccacaacaa     1140
cgtatcgttg ctcaactagg tcaggtgtc tacagaacct tgtcttccac cttgtacaga      1200
agacccttca atatcggtat caacaaccag caactttccg ttcttgacgg aacagagttc     1260
gcctatggaa cctcttctaa cttgccatcc gctgtttaca gaaagagcgg aaccgttgat     1320
tccttggacg aaatcccacc acagaacaac aatgtgccac ccaggcaagg attctcccac     1380
aggttgagcc acgtgtccat gttccgttcc ggattcagca acagttccgt gagcatcatc     1440
agagctccta tgttctcttg gatacaccgt agtgctgagt tcaacaacat catcgcatcc     1500
gatagtatta ctcaaatccc tgcagtgaag ggaaactttc tcttcaacgg ttctgtcatt     1560
tcaggaccag gattcactgg tggagacctc gttagactca acagcagtgg aaataacatt     1620
cagaatagag ggtatattga agttccaatt cacttcccat ccacatctac cagatataga     1680
gttcgtgtga ggtatgcttc tgtgacccct attcacctca acgttaattg gggtaattca     1740
tccatcttct ccaatacagt tccagctaca gctacctcct tggataatct ccaatccagc     1800
gatttcggtt actttgaaag tgccaatgct tttacatctt cactcggtaa catcgtgggt     1860 gttagaaaact ttagtgggac tgcaggagtg attatcgaca gattcgagtt cattccagtt     1920
actgcaacac tcgaggctga atgagaattc aaaggcctac gtcgacgagc tcactagtcg     1980
cggccgcttt cgaatctaga gcctgcagtc tcgaggcatg cggtaccaag cttgtcgaga     2040
agtactagag gatcataatc ag                                              2062
```

<210> SEQ ID NO 3
<211> LENGTH: 956
<212> TYPE: DNA
<213> ORGANISM: Artificial Sequence
<220> FEATURE:
<223> OTHER INFORMATION: Description of Artificial Sequence: Nucleotide sequence of RTB1 in pFASTBAC1

<400> SEQUENCE: 3

```
aaataagtat tttactgttt tcgtaacagt tttgtaataa aaaaacctat aaatattccg       60
gattattcat accgtcccac catcgggcgc ggatcccggt ccgaagcgcg cggaattcat      120
gctgatgttt gtatggatcc tgagcccata gtgcgtatcg taggtcgaaa tggtctatgt      180
gttgatgtta gggatggaag attccacaac ggaaacgcaa tacagttgtg gccatgcaag     240
tctaatacag atgcaaatca gctctggact ttgaaaagag acaatactat tcgatctaat      300
ggaaagtgtt taactactta cgggtacagt ccggagtct atgtgatgat ctatgattgc      360
aatactgctg caactgatgc cacccgctgg caaatatggg ataatggaac catcataaat      420
cccagatcta gtctagtttt agcagcgaca tcagggaaca gtggtaccac acttacggtg     480
caaaccaaca tttatgccgt tagtcaaggt tggcttccta ctaataatac acaaccttt     540 gttacaacca ttgttgggct atatggtctg tgcttgcaag caaatagtgg acaagtatgg     600
atagaggact gtagcagtga aaaggctgaa caacagtggg ctctttatgc agatggttca    660
atacgtcctc agcaaaaccg agataattgc cttacaagtg attctaatat acgggaaaca    720
```

-continued

```
gttgtcaaga tcctctcttg tggccctgca tcctctggcc aacgatggat gttcaagaat    780
gatggaacca ttttaaattt gtatagtggg ttggtgttag atgtgagggc atcggatccg    840
agccttaaac aaatcattct ttaccctctc catggtgacc caaaccaaat atggttacca    900
ttattttgat agacagatta caagcttgtc gagaagtact agaggatcat aatcag        956
```

<210> SEQ ID NO 4
<211> LENGTH: 860
<212> TYPE: DNA
<213> ORGANISM: Artificial Sequence
<220> FEATURE:
<223> OTHER INFORMATION: Description of Artificial Sequence: Nucleotide sequence of RTB2 in pFASTBAC1

<400> SEQUENCE: 4

```
aaataagtat tttactgttt tcgtaacagt tttgtaataa aaaaacctat aaatattccg     60
gattattcat accgtcccac catcgggcgc ggatcccggt ccgaagcgcg cggaattcat    120
gctgatgttt gtatggatcc tgagcccata gtgcgtatcg taggtcgaaa tggtctatgt    180
gttgatgtta gggatggaag attccacaac ggaaacgcaa tacagttgtg gccatgcaag    240
tctaatacag atgcaaatca gctctggact ttgaaaagag acaatactat tcgatctaat    300
ggaaagtgtt taactactta cgggtacagt ccgggagtct atgtgatgat ctatgattgc    360
aatactgctg caactgatgc cacccgctgg caaatatggg ataatggaac catcataaat    420
cccagatcta gtctagtttt agcagcgaca tcagggaaca gtggtaccac acttacggtg    480
caaaccaaca tttatgccgt tagtcaaggt tggcttccta ctaataatac acaaccttt    540 gttacaacca ttgttgggct atatggtctg tgcttgcaag caaatagtgg acaagtatgg    600
atagaggact gtagcagtga aaaggctgaa caacagtggg ctctttatgc agatggttca    660
atacgtcctc agcaaaaccg agataattgc cttacaagtg attctaatat acgggaaaca    720
gttgtcaaga tcctctcttg tggccctgca tcctctggcc aacgatggat gttcaagaat    780
gatggaacca ttttaaattt gtatagtggg ttggtgttag atgtgaagct tgtcgagaag    840
tactagagga tcataatcag                                                860
```

<210> SEQ ID NO 5
<211> LENGTH: 604
<212> TYPE: DNA
<213> ORGANISM: Artificial Sequence
<220> FEATURE:
<223> OTHER INFORMATION: Description of Artificial Sequence: Nucleotide sequence of RTB3 in pFASTBAC1

<400> SEQUENCE: 5

```
aaataagtat tttactgttt tcgtaacagt tttgtaataa aaaaacctat aaatattccg     60
gattattcat accgtcccac catcgggcgc ggatcccggt ccgaagcgcg cggaattcat    120
gctgatgttt gtatggatcc tgagcccata gtgcgtatcg taggtcgaaa tggtctatgt    180
gttgatgtta gggatggaag attccacaac ggaaacgcaa tacagttgtg gccatgcaag    240
tctaatacag atgcaaatca gctctggact ttgaaaagag acaatactat tcgatctaat    300
ggaaagtgtt taactactta cgggtacagt ccgggagtct atgtgatgat ctatgattgc    360
aatactgctg caactgatgc cacccgctgg caaatatggg ataatggaac catcataaat    420
cccagatcta gtctagtttt agcagcgaca tcagggaaca gtggtaccac acttacggtg    480
caaaccaaca tttatgccgt tagtcaaggt tggcttccta ctaataatac acaaccttt    540 gttacaacca ttgttgggct atatggtcta agcttgtcga gaagtactag aggatcataa    600
```

-continued tcag                                                                    604

<210> SEQ ID NO 6
<211> LENGTH: 2788
<212> TYPE: DNA
<213> ORGANISM: Artificial Sequence
<220> FEATURE:
<223> OTHER INFORMATION: Description of Artificial Sequence: Nucleotide
      sequence of CryIA(b)-RTB1 in pFASTBAC1

<400> SEQUENCE: 6
aaataagtat tttactgttt tcgtaacagt tttgtaataa aaaaacctat aaatattccg    60
gattattcat accgtcccac catcgggcgc ggatccatgg acaacaaccc aaacatcaac   120
gaatgcattc catacaactg cttgagtaac ccagaagttg aagtacttgg tggagaacgc   180
attgaaaccg gttacactcc catcgacatc tccttgtcct tgacacagtt tctgctcagc   240
gagttcgtgc caggtgctgg gttcgttctc ggactagttg acatcatctg gggtatcttt   300
ggtccatctc aatgggatgc attcctggtg caaattgagc agttgatcaa ccagaggatc   360
gaagagttcg ccaggaacca ggccatctct aggttggaag gattgagcaa tctctaccaa   420
atctatgcag agagcttcag agagtgggaa gccgatccta ctaacccagc tctccgcgag   480
gaaatgcgta ttcaattcaa cgacatgaac agcgccttga ccacagctat cccattgttc   540
gcagtccaga actaccaagt tcctctcttg tccgtgtacg ttcaagcagc taatcttcac   600
ctcagcgtgc ttcgagacgt tagcgtgttt gggcaaaggt ggggattcga tgctgcaacc   660
atcaatagcc gttacaacga ccttactagg ctgattggaa actacaccga ccacgctgtt   720
cgttggtaca acactggctt ggagcgtgtc tggggtcctg attctagaga ttggattaga   780
tacaaccagt tcaggagaga attgaccctc acagttttgg acattgtgtc tctcttcccg   840
aactatgact ccagaaccta ccctatccgt acagtgtccc aacttaccag agaaatctat   900
actaacccag ttcttgagaa cttcgacggt agcttccgtg ttctgcccca aggtatcgaa   960
ggctccatca ggagcccaca cttgatggac atcttgaaca gcataactat ctacaccgat  1020
gctcacagag gagagtatta ctggtctgga caccagatca tggcctctcc agttggattc  1080
agcgggcccg agtttacctt tcctctctat ggaactatgg gaaacgccgc tccacaacaa  1140
cgtatcgttg ctcaactagg tcagggtgtc tacagaacct tgtcttccac cttgtacaga  1200
agacccttca atatcggtat caacaaccag caactttccg ttcttgacgg aacagagttc  1260
gcctatggaa cctcttctaa cttgccatcc gctgtttaca gaaagagcgg aaccgttgat  1320
tccttggacg aaatcccacc acagaacaac aatgtgccac ccaggcaagg attctcccac  1380
aggttgagcc acgtgtccat gttccgttcc ggattcagca cagttccgt gagcatcatc  1440 agagctccta tgttctcatg gattcatcgt agtgctgagt tcaacaatat cattccttcc  1500
tctcaaatca cccaaatccc attgaccaag tctactaacc ttggatctgg aacttctgtc  1560
gtgaaaggac caggcttcac aggaggtgat attcttagaa gaacttctcc tggccagatt  1620
agcaccctca gagttaacat cactgcacca ctttctcaaa gatatcgtgt caggattcgt  1680
tacgcatcta ccactaactt gcaattccac acctccatcg acggaaggcc tatcaatcag  1740
ggtaacttct ccgcaaccat gtcaagcggc agcaacttgc aatccggcag cttcagaacc  1800
gtcggtttca ctactccttt caacttctct aacggatcaa gcgttttcac ccttagcgct  1860
catgtgttca attctggcaa tgaagtgtac attgaccgta ttgagtttgt gcctgccgaa  1920
gttaccttcg aggctgagta ctgagaattc atgctgatgt ttgtatggat cctgagccca  1980

```
tagtgcgtat cgtaggtcga aatggtctat gtgttgatgt tagggatgga agattccaca    2040
acggaaacgc aatacagttg tggccatgca agtctaatac agatgcaaat cagctctgga    2100
ctttgaaaag agacaatact attcgatcta atggaaagtg tttaactact tacgggtaca    2160
gtccgggagt ctatgtgatg atctatgatt gcaatactgc tgcaactgat gccacccgct    2220
ggcaaatatg gataatgga accatcataa atcccagatc tagtctagtt ttagcagcga    2280
catcagggaa cagtggtacc acacttacgg tgcaaaccaa catttatgcc gttagtcaag    2340
gttggcttcc tactaataat acacaacctt tgttacaac cattgttggg ctatatggtc    2400
tgtgcttgca agcaaatagt ggacaagtat ggatagagga ctgtagcagt gaaaaggctg    2460
aacaacagtg ggctctttat gcagatggtt caatacgtcc tcagcaaaac cgagataatt    2520
gccttacaag tgattctaat atacgggaaa cagttgttaa gatcctctct tgtggccctg    2580
catcctctgg ccaacgatgg atgttcaaga atgatggaac catttttaaat ttgtatagtg    2640 gattggtgtt agatgtgagg cgatcggatc cgagccttaa acaaatcatt ctttacccctc    2700 tccatggtga cccaaaccaa atatggttac cattattttg atagacagat tacaagcttg    2760
tcgagaagta ctagaggatc ataatcag                                       2788

<210> SEQ ID NO 7
<211> LENGTH: 2692
<212> TYPE: DNA
<213> ORGANISM: Artificial Sequence
<220> FEATURE:
<223> OTHER INFORMATION: Description of Artificial Sequence: Nucleotide
      sequence of CryIA(b)-RTB2 in pFASTBAC1

<400> SEQUENCE: 7
aaataagtat tttactgttt tcgtaacagt tttgtaataa aaaaacctat aaatattccg      60
gattattcat accgtcccac catcgggcgc ggatccatgg acaacaaccc aaacatcaac    120
gaatgcattc catacaactg cttgagtaac ccagaagttg aagtacttgg tggagaacgc    180
attgaaaccg gttacactcc catcgacatc tccttgtcct tgacacagtt tctgctcagc    240
gagttcgtgc caggtgctgg gttcgttctc ggactagttg acatcatctg gggtatcttt    300
ggtccatctc aatgggatgc attcctggtg caaattgagc agttgatcaa ccagaggatc    360
gaagagttcg ccaggaacca ggccatctct aggttggaag gattgagcaa tctctaccaa    420
atctatgcag agagcttcag agagtgggaa gccgatccta ctaacccagc tctccgcgag    480
gaaatgcgta ttcaattcaa cgacatgaac agcgccttga ccacagctat cccattgttc    540
gcagtccaga actaccaagt tcctctcttg tccgtgtacg ttcaagcagc taatcttcac    600
ctcagcgtgc ttcgagacgt tagcgtgttt ggcaaaggt ggggattcga tgctgcaacc    660
atcaatagcc gttacaacga ccttactagg ctgattggaa actacaccga ccacgctgtt    720
cgttggtaca cactggcttg gagcgtgtc tgggtcctg attctagaga ttggattaga    780
tacaaccagt tcaggagaga attgaccctc acagttttgg acattgtgtc tctcttcccg    840
aactatgact ccagaaccta cccgtatcgt acagtgtccc aacttaccag agaaatctat    900
actaacccag ttcttgagaa cttcgacggt agcttccgtg ttctgcccca aggtatcgaa    960
ggctccatca ggagcccaca cttgatggac atccttgaaca gcataactat ctacaccgat    1020
gctcacagag gagagtatta ctggtctgga caccagatca tggcctctcc agttggattc    1080
agcgggcccg agtttaccct tcctctctat ggaactatgg aaacgccgc tccacaacaa    1140 cgtatcgttg ctcaactagg tcagggtgtc tacagaacct tgtcttccac cttgtacaga    1200
```

-continued

```
agacccttca atatcggtat caacaaccag caactttccg ttcttgacgg aacagagttc   1260
gcctatggaa cctcttctaa cttgccatcc gctgtttaca gaaagagcgg aaccgttgat   1320
tccttggacg aaatcccacc acagaacaac aatgtgccac ccaggcaagg attctcccac   1380
aggttgagcc acgtgtccat gttccgttcc ggattcagca acagttccgt gagcatcatc   1440
agagctccta tgttctcatg gattcatcgt agtgctgagt tcaacaatat cattccttcc   1500
tctcaaatca cccaaatccc attgaccaag tctactaacc ttggatctgg aacttctgtc   1560
gtgaaaggac caggcttcac aggaggtgat attcttagaa gaacttctcc tggccagatt   1620
agcaccctca gagttaacat cactgcacca ctttctcaaa gatatcgtgt caggattcgt   1680
tacgcatcta ccactaactt gcaattccac acctccatcg acggaaggcc tatcaatcag   1740
ggtaacttct ccgcaaccat gtcaagcggc agcaacttgc aatccggcag cttcagaacc   1800
gtcggtttca ctactccttt caacttctct aacggatcaa gcgttttcac ccttagcgct   1860
catgtgttca attctggcaa tgaagtgtac attgaccgta ttgagtttgt gcctgccgaa   1920
gttaccttcg aggctgagta ctgagaattc atgctgatgt ttgtatggat cctgagccca   1980
tagtgcgtat cgtaggtcga aatggtctat gtgttgatgt tagggatgga agattccaca   2040
acggaaacgc aatacagttg tggccatgca agtctaatac agatgcaaat cagctctgga   2100
ctttgaaaag agacaatact attcgatcta atggaaagtg tttaactact tacgggtaca   2160
gtccgggagt ctatgtgatg atctatgatt gcaatactgc tgcaactgat gccacccgct   2220
ggcaaatatg ggataatgga accatcataa atcccagatc tagtctagtt ttagcagcga   2280
catcagggaa cagtggtacc acacttacgg tgcaaaccaa catttatgcc gttagtcaag   2340
gttggcttcc tactaataat acacaacctt ttgttacaac cattgttggg ctatatggtc   2400
tgtgcttgca agcaaatagt ggacaagtat ggatagagga ctgtagcagt gaaaaggctg   2460
aacaacagtg ggctctttat gcagatggtt caatacgtcc tcagcaaaac cgagataatt   2520
gccttacaag tgattctaat atacgggaaa cagttgttaa gatcctctct tgtggccctg   2580
catcctctgg ccaacgatgg atgttcaaga atgatggaac cattttaaat ttgtatagtg   2640
gattggtgtt agatgtgaag cttgtcgaga agtactagag gatcataatc ag           2692
```

```

<210> SEQ ID NO 8
<211> LENGTH: 2436
<212> TYPE: DNA
<213> ORGANISM: Artificial Sequence
<220> FEATURE:
<223> OTHER INFORMATION: Description of Artificial Sequence: Nucleotide
      sequence of CryIA(b)-RTB3 in pFASTBAC1

<400> SEQUENCE: 8

```

```
aaataagtat tttactgttt tcgtaacagt tttgtaataa aaaaacctat aaatattccg     60
gattattcat accgtcccac catcgggcgc ggatccatgg acaacaaccc aaacatcaac    120
gaatgcattc catacaactg cttgagtaac ccagaagttg aagtacttgg tggagaacgc    180
attgaaaccg gttacactcc catcgacatc tccttgtcct tgacacagtt tctgctcagc    240
gagttcgtgc caggtgctgg gttcgttctc ggactagttg acatcatctg ggtatcttt     300
ggtccatctc aatgggatgc attcctggtg caaattgagc agttgatcaa ccagaggatc    360
gaagagttcg ccaggaacca ggccatctct aggttggaag gattgagcaa tctctaccaa    420
atctatgcag agagcttcag agagtgggaa gccgatccta ctaacccagc tctccgcgag    480
gaaatgcgta ttcaattcaa cgacatgaac agcgccttga ccacagctat cccattgttc    540
```

-continued gcagtccaga actaccaagt tcctctcttg tccgtgtacg ttcaagcagc taatcttcac 600
ctcagcgtgc ttcgagacgt tagcgtgttt gggcaaaggt ggggattcga tgctgcaacc 660
atcaatagcc gttacaacga ccttactagg ctgattggaa actacaccga ccacgctgtt 720
cgttggtaca acactggctt ggagcgtgtc tggggtcctg attctagaga ttggattaga 780
tacaaccagt tcaggagaga attgaccctc acagttttgg acattgtgtc tctcttcccg 840
aactatgact ccagaaccta ccctatccgt acagtgtccc aacttaccag agaaatctat 900
actaacccag ttcttgagaa cttcgacggt agcttccgtg gttctgccca aggtatcgaa 960
ggctccatca ggagcccaca cttgatggac atcttgaaca gcataactat ctacaccgat 1020
gctcacagag gagagtatta ctggtctgga caccagatca tggcctctcc agttggattc 1080
agcgggcccg agtttacctt tcctctctat ggaactatgg gaaacgccgc tccacaacaa 1140
cgtatcgttg ctcaactagg tcagggtgtc tacagaacct tgtcttccac cttgtacaga 1200
agacccttca atatcggtat caacaaccag caactttccg ttcttgacgg aacagagttc 1260
gcctatggaa cctcttctaa cttgccatcc gctgtttaca gaaagagcgg aaccgttgat 1320
tccttggacg aaatcccacc acagaacaac aatgtgccac ccaggcaagg attctcccac 1380
aggttgagcc acgtgtccat gttccgttcc ggattcagca acagttccgt gagcatcatc 1440
agagctccta tgttctcatg gattcatcgt agtgctgagt tcaacaatat cattccttcc 1500
tctcaaatca cccaaatccc attgaccaag tctactaacc ttggatctgg aacttctgtc 1560
gtgaaaggac caggcttcac aggaggtgat attcttagaa gaacttctcc tggccagatt 1620
agcaccctca gagttaacat cactgcacca ctttctcaaa gatatcgtgt caggattcgt 1680
tacgcatcta ccactaactt gcaattccac acctccatcg acggaaggcc tatcaatcag 1740
ggtaacttct ccgcaaccat gtcaagcggc agcaacttgc aatccggcag cttcagaacc 1800
gtcggtttca ctactccttt caacttctct aacggatcaa gcgttttcac ccttagcgct 1860
catgtgttca attctggcaa tgaagtgtac attgaccgta ttgagtttgt gcctgccgaa 1920
gttaccttcg aggctgagta ctgagaattc atgctgatgt ttgtatggat cctgagccca 1980
tagtgcgtat cgtaggtcga aatggtctat gtgttgatgt tagggatgga agattccaca 2040
acggaaacgc aatacagttg tggccatgca agtctaatac agatgcaaat cagctctgga 2100
ctttgaaaag agacaatact attcgatcta atggaaagtg tttaactact tacgggtaca 2160
gtccgggagt ctatgtgatg atctatgatt gcaatactgc tgcaactgat gccacccgct 2220
ggcaaatatg ggataatgga accatcataa atcccagatc tagtctagtt ttagcagcga 2280
catcagggaa cagtggtacc acacttacgg tgcaaaccaa catttatgcc gttagtcaag 2340
gttggcttcc tactaataat acacaacctt ttgttacaac cattgttggg ctatatggtc 2400
taagcttgtc gagaagtact agaggatcat aatcag 2436

<210> SEQ ID NO 9
<211> LENGTH: 2788
<212> TYPE: DNA
<213> ORGANISM: Artificial Sequence
<220> FEATURE:
<223> OTHER INFORMATION: Description of Artificial Sequence: Nucleotide
sequence of CryIA(c)-RTB1 in pFASTBAC1

<400> SEQUENCE: 9
aaataagtat tttactgttt tcgtaacagt tttgtaataa aaaaacctat aaatattccg 60
gattattcat accgtcccac catcgggcgc ggatccatgg acaacaaccc aaacatcaac 120

-continued

```
gaatgcattc catacaactg cttgagtaac ccagaagttg aagtacttgg tggagaacgc      180
attgaaaccg gttacactcc catcgacatc tccttgtcct tgacacagtt tctgctcagc      240
gagttcgtgc caggtgctgg gttcgttctc ggactagttg acatcatctg gggtatctttt     300 ggtccatctc aatgggatgc attcctggtg caaattgagc agttgatcaa ccagaggatc      360
gaagagttcg ccaggaacca ggccatctct aggttggaag gattgagcaa tctctaccaa      420
atctatgcag agagcttcag agagtgggaa gccgatccta ctaacccagc tctccgcgag      480
gaaatgcgta ttcaattcaa cgacatgaac agcgccttga ccacagctat cccattgttc      540
gcagtccaga actaccaagt tcctctcttg tccgtgtacg ttcaagcagc taatcttcac      600
ctcagcgtgc ttcgagacgt tagcgtgttt gggcaaaggt gggattcga tgctgcaacc      660 atcaatagcc gttacaacga ccttactagg ctgattggaa actacaccga ccacgctgtt      720
cgttggtaca acactggctt ggagcgtgtc tgggtcctg attctagaga ttggattaga       780
tacaaccagt tcaggagaga attgaccctc acagttttgg acattgtgtc tctcttcccg      840
aactatgact ccagaaccta ccctatccgt acagtgtccc aacttaccag agaaatctat      900
actaacccag ttcttgagaa cttcgacggt agcttccgtg gttctgccca aggtatcgaa      960
ggctccatca ggagcccaca cttgatggac atcttgaaca gcataactat ctacaccgat     1020
gctcacagag gagagtatta ctggtctgga caccagatca tggcctctcc agttggattc     1080
agcgggcccg agtttacctt tcctctctat ggaactatgg gaaacgccgc tccacaacaa     1140
cgtatcgttg ctcaactagg tcaggtgtc tacagaacct tgtcttccac cttgtacaga      1200
agacccttca atatcggtat caacaaccag caactttccg ttcttgacgg aacagagttc     1260
gcctatggaa ccctcttctaa cttgccatcc gctgtttaca gaaagagcgg aaccgttgat     1320
tccttggacg aaatcccacc acagaacaac aatgtgccac ccaggcaagg attctcccac     1380
aggttgagcc acgtgtccat gttccgttcc ggattcagca acagttccgt gagcatcatc     1440
agagctccta tgttctcttg gatacaccgt agtgctgagt tcaacaacat catcgcatcc     1500
gatagtatta ctcaaatccc tgcagtgaag ggaaactttc tcttcaacgg ttctgtcatt     1560
tcaggaccag gattcactgg tggagacctc gttagactca acagcagtgg aaataacatt     1620
cagaatagag ggtatattga agttccaatt cacttcccat ccacatctac cagatataga     1680
gttcgtgtga ggtatgcttc tgtgaccct attcacctca cgttaattg gggtaattca       1740 tccatcttct ccaatacagt tccagctaca gctacctcct tggataatct ccaatccagc     1800
gatttcggtt acttttgaaag tgccaatgct tttacatctt cactcggtaa catcgtgggt     1860
gttagaaact ttagtgggac tgcaggagtg attatcgaca gattcgagtt cattccagtt     1920
actgcaacac tcgaggctga atgagaattc atgctgatgt ttgtatggat cctgagccca     1980
tagtgcgtat cgtaggtcga aatggtctat gtgttgatgt tagggatgga agattccaca    2040
acggaaacgc aatacagttg tggccatgca agtctaatac agatgcaaat cagctctgga    2100
ctttgaaaag agacaatact attcgatcta atggaaagtg tttaactact tacgggtaca    2160
gtccgggagt ctatgtgatg atctatgatt gcaatactgc tgcaactgat gccacccgct    2220
ggcaaatatg gataatgga accatcataa atcccagatc tagtctagtt ttagcagcga     2280
catcagggaa cagtggtacc acacttacgg tgcaaaccaa catttatgcc gttagtcaag    2340
gttggcttcc tactaataat acacaacctt tgttacaac cattgttggg ctatatggtc     2400
tgtgcttgca agcaaatagt ggacaagtat ggatagagga ctgtagcagt gaaaaggctg    2460
```

```
aacaacagtg ggctctttat gcagatggtt caatacgtcc tcagcaaaac cgagataatt     2520
gccttacaag tgattctaat atacgggaaa cagttgttaa gatcctctct tgtggccctg     2580
catcctctgg ccaacgatgg atgttcaaga atgatggaac catttttaaat ttgtatagtg    2640 gattggtgtt agatgtgagg cgatcggatc cgagccttaa acaaatcatt ctttaccctc     2700
tccatggtga cccaaaccaa atatggttac cattattttg atagacagat tacaagcttg     2760
tcgagaagta ctagaggatc ataatcag                                         2788
```

<210> SEQ ID NO 10
<211> LENGTH: 2692
<212> TYPE: DNA
<213> ORGANISM: Artificial Sequence
<220> FEATURE:
<223> OTHER INFORMATION: Description of Artificial Sequence: Nucleotide
      sequence of CryIA(c)-RTB2 in pFASTBAC1

<400> SEQUENCE: 10

```
aaataagtat tttactgttt tcgtaacagt tttgtaataa aaaaacctat aaatattccg       60
gattattcat accgtcccac catcgggcgc ggatccatgg acaacaaccc aaacatcaac     120
gaatgcattc catacaactg cttgagtaac ccagaagttg aagtacttgg tggagaacgc     180
attgaaaccg gttacactcc catcgacatc tccttgtcct tgacacagtt tctgctcagc     240
gagttcgtgc caggtgctgg gttcgttctc ggactagttg acatcatctg gggtatcttt     300
ggtccatctc aatgggatgc attcctggtg caaattgagc agttgatcaa ccagaggatc     360
gaagagttcg ccaggaacca ggccatctct aggttggaag gattgagcaa tctctaccaa     420
atctatgcag agagcttcag agagtgggaa gccgatccta ctaacccagc tctccgcgag     480
gaaatgcgta ttcaattcaa cgacatgaac agcgccttga ccacagctat cccattgttc     540
gcagtccaga actaccaagt tcctctcttg tccgtgtacg ttcaagcagc taatcttcac     600
ctcagcgtgc ttcgagacgt tagcgtgttt gggcaaaggt ggggattcga tgctgcaacc     660
atcaatagcc gttacaacga ccttactagg ctgattggaa actacaccga ccacgctgtt     720
cgttggtaca cactggcttg gagcgtgtc tggggtcctg attctagaga ttggattaga     780
tacaaccagt tcaggagaga attgaccctc acagttttgg acattgtgtc tctcttcccg     840
aactatgact ccagaaccta ccctatccgt acagtgtccc aacttaccag agaaatctat     900
actaacccag ttcttgagaa cttcgacggt agcttccgtg ttctgcccca aggtatcgaa     960
ggctccatca ggagcccaca cttgatggac atcttgaaca gcataactat ctacaccgat    1020
gctcacagag gagagtatta ctggtctgga caccagatca tggcctctcc agttggattc    1080
agcgggcccg agtttacctt tcctctctat ggaactatgg gaaacgccgc tccacaacaa    1140
cgtatcgttg ctcaactagg tcagggtgtc tacagaacct tgtcttccac cttgtacaga    1200
agacccttca atatcggtat caacaaccag caactttccg ttcttgacgg aacagagttc    1260
gcctatggaa cctcttctaa cttgccatcc gctgtttaca gaaagagcgg aaccgttgat    1320
tccttggacg aaatcccacc acagaacaac aatgtgccac ccaggcaagg attctcccac    1380
aggttgagcc acgtgtccat gttccgttcc ggattcagca acagttccgt gagcatcatc    1440
agagctccta tgttctcttg gatacaccgt agtgctgagt tcaacaacat catcgcatcc    1500
gatagtatta ctcaaatccc tgcagtgaag ggaaactttc tcttcaacgg ttctgtcatt    1560
tcaggaccag gattcactgg tggagaccct gttagactca acagcagtgg aaataacatt    1620
cagaatagag ggtatattga agttccaatt cacttcccat ccacatctac cagatataga    1680
```

```
gttcgtgtga ggtatgcttc tgtgacccct attcacctca acgttaattg gggtaattca    1740
tccatcttct ccaatacagt tccagctaca gctacctcct tggataatct ccaatccagc    1800
gatttcggtt actttgaaag tgccaatgct tttacatctt cactcggtaa catcgtgggt    1860
gttagaaact ttagtgggac tgcaggagtg attatcgaca gattcgagtt cattccagtt    1920
actgcaacac tcgaggctga atgagaattc atgctgatgt ttgtatggat cctgagccca    1980
tagtgcgtat cgtaggtcga atggtctat gtgttgatgt tagggatgga agattccaca    2040
acggaaacgc aatacagttg tggccatgca agtctaatac agatgcaaat cagctctgga    2100
ctttgaaaag agacaatact attcgatcta atggaaagtg tttaactact tacgggtaca    2160
gtccgggagt ctatgtgatg atctatgatt gcaatactgc tgcaactgat gccacccgct    2220
ggcaaatatg ggataatgga accatcataa atcccagatc tagtctagtt ttagcagcga    2280
catcagggaa cagtggtacc acacttacgg tgcaaaccaa catttatgcc gttagtcaag    2340
gttggcttcc tactaataat acacaacctt ttgttacaac cattgttggg ctatatggtc    2400
tgtgcttgca agcaaatagt ggacaagtat ggatagagga ctgtagcagt gaaaaggctg    2460
aacaacagtg ggctctttat gcagatggtt caatacgtcc tcagcaaaac cgagataatt    2520
gccttacaag tgattctaat atacgggaaa cagttgttaa gatcctctct tgtggccctg    2580
catcctctgg ccaacgatgg atgttcaaga atgatggaac cattttaaat ttgtatagtg    2640
gattggtgtt agatgtgaag cttgtcgaga agtactagag gatcataatc ag           2692
```

<210> SEQ ID NO 11
<211> LENGTH: 2436
<212> TYPE: DNA
<213> ORGANISM: Artificial Sequence
<220> FEATURE:
<223> OTHER INFORMATION: Description of Artificial Sequence: Nucleotide
      sequence of CryIA(c)-RTB3 in pFASTBAC1

<400> SEQUENCE: 11
aaataagtat tttactgttt tcgtaacagt tttgtaataa aaaaacctat aaatattccg 60
gattattcat accgtcccac catcgggcgc ggatccatgg acaacaaccc aaacatcaac 120
gaatgcattc catacaactg cttgagtaac ccagaagttg aagtacttgg tggagaacgc 180
attgaaaccg gttacactcc catcgacatc tccttgtcct tgacacagtt tctgctcagc 240
gagttcgtgc caggtgctgg gttcgttctc ggactagttg acatcatctg ggtatcttt 300 ggtccatctc aatgggatgc attcctggtg caaattgagc agttgatcaa ccagaggatc 360
gaagagttcg ccaggaacca ggccatctct aggttggaag gattgagcaa tctctaccaa 420
atctatgcag agagcttcag agagtgggaa gccgatccta ctaacccagc tctccgcgag 480
gaaatgcgta ttcaattcaa cgacatgaac agcgccttga ccacagctat cccattgttc 540
gcagtccaga actaccaagt tcctctcttg tccgtgtacg ttcaagcagc taatcttcac 600
ctcagcgtgc ttcgagacgt tagcgtgttt gggcaaaggt ggggattcga tgctgcaacc 660
atcaatagcc gttacaacga ccttactagg ctgattggaa actacaccga ccacgctgtt 720
cgttggtaca acactggctt ggagcgtgtc tggggtcctg attctagaga ttggattaga 780
tacaaccagt tcaggagaga attgaccctc acagttttgg acattgtgtc tctcttcccg 840
aactatgact ccagaaccta ccctatccgt acagtgtccc aacttaccag agaaatctat 900
actaacccag ttcttgagaa cttcgacggt agcttccgtg gttctgccca aggtatcgaa 960
ggctccatca ggagcccaca cttgatggac atcttgaaca gcataactat ctacaccgat 1020

```
gctcacagag gagagtatta ctggtctgga caccagatca tggcctctcc agttggattc    1080
agcgggcccg agtttacctt tcctctctat ggaactatgg gaaacgccgc tccacaacaa    1140
cgtatcgttg ctcaactagg tcaggtgtc tacagaacct tgtcttccac cttgtacaga     1200
agacccttca atatcggtat caacaaccag caactttccg ttcttgacgg aacagagttc    1260
gcctatggaa cctcttctaa cttgccatcc gctgtttaca gaaagagcgg aaccgttgat    1320
tccttggacg aaatcccacc acagaacaac aatgtgccac ccaggcaagg attctcccac    1380
aggttgagcc acgtgtccat gttccgttcc ggattcagca acagttccgt gagcatcatc    1440
agagctccta tgttctcttg gatacaccgt agtgctgagt caacaacat catcgcatcc     1500 gatagtatta ctcaaatccc tgcagtgaag ggaaactttc tcttcaacgg ttctgtcatt    1560
tcaggaccag gattcactgg tggagacctc gttagactca acagcagtgg aaataacatt    1620
cagaatagag ggtatattga agttccaatt cacttcccat ccacatctac cagatataga    1680
gttcgtgtga ggtatgcttc tgtgaccct attcacctca acgttaattg gggtaattca    1740
tccatcttct ccaatacagt tccagctaca gctacctcct tggataatct ccaatccagc    1800
gatttcggtt actttgaaag tgccaatgct tttacatctt cactcggtaa catcgtgggt    1860
gttagaaact ttagtgggac tgcaggagtg attatcgaca gattcgagtt cattccagtt    1920
actgcaacac tcgaggctga atgagaattc atgctgatgt ttgtatggat cctgagccca    1980
tagtgcgtat cgtaggtcga aatggtctat gtgttgatgt tagggatgga agattccaca    2040
acggaaacgc aatacagttg tggccatgca agtctaatac agatgcaaat cagctctgga    2100
ctttgaaaag agacaatact attcgatcta atggaaagtg tttaactact tacgggtaca    2160
gtccgggagt ctatgtgatg atctatgatt gcaatactgc tgcaactgat gccacccgct    2220
ggcaaatatg ggataatgga accatcataa atcccagatc tagtctagtt ttagcagcga    2280
catcagggaa cagtggtacc acacttacgg tgcaaaccaa catttatgcc gttagtcaag    2340
gttggcttcc tactaataat acacaacctt ttgttacaac cattgttggg ctatatggtc    2400
taagcttgtc gagaagtact agaggatcat aatcag                              2436
```

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 12

```
caacaacaaa ggaattcatg ctgatg                                           26
```

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 13

```
ggacacacac actgcaagct tgtaatc                                          27
```

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

```
<400> SEQUENCE: 14
cggatccgaa agcttcacat ctaacac                                              27

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 15
gcttgcaagc ttagaccata tagccc                                               26

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 16
cgcattgaaa ccggttacac tccca                                                25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
cttgggcaga accacggaag ctacc                                                25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 18
gatgtttgta tggatcctca gccca                                                25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
gccgaacaat ggttgtaaca aaagg                                                25
```